United States Patent [19]
McVey et al.

[11] Patent Number: 6,063,627
[45] Date of Patent: *May 16, 2000

[54] METHODS AND VECTORS FOR SITE-SPECIFIC RECOMBINATION

[75] Inventors: Duncan L. McVey, Derwood; Imre Kovesdi, Rockville, both of Md.

[73] Assignee: GenVec, Inc., Gaithersburg, Md.

[ * ] Notice: This patent is subject to a terminal disclaimer.

[21] Appl. No.: 09/030,563

[22] Filed: Feb. 25, 1998

Related U.S. Application Data

[63] Continuation of application No. PCT/US96/14123, Aug. 27, 1996, which is a continuation-in-part of application No. 08/522,684, Sep. 1, 1995, Pat. No. 5,801,030.

[51] Int. Cl.[7] ........................... C12N 15/90; C12N 15/79; C12N 15/34
[52] U.S. Cl. ..................... 435/440; 435/455; 435/320.1; 536/23.1; 536/23.72; 536/24.1
[58] Field of Search ................................ 435/455, 320.1, 435/440; 536/23.1, 23.72, 24.1

[56] References Cited

U.S. PATENT DOCUMENTS

| | | | |
|---|---|---|---|
| 4,562,155 | 12/1985 | Ricciardi et al. | 435/91.1 |
| 4,797,368 | 1/1989 | Carter et al. | 435/320.1 |
| 4,959,317 | 9/1990 | Sauer | 435/462 |
| 5,173,414 | 12/1992 | Lebkowski et al. | 435/91.4 |

FOREIGN PATENT DOCUMENTS

| | | |
|---|---|---|
| 0704534 | 4/1996 | European Pat. Off. . |
| 0732405 | 9/1996 | European Pat. Off. . |
| WO 92/15694 | 9/1992 | WIPO . |
| WO 94/12629 | 6/1994 | WIPO . |
| WO 94/17176 | 8/1994 | WIPO . |
| WO 95/11984 | 5/1995 | WIPO . |
| WO 95/13377 | 5/1995 | WIPO . |
| WO 95/23867 | 9/1995 | WIPO . |

OTHER PUBLICATIONS

Kellendonk et al. Regulation of Cre recombinase activity by the synthetic steroid RU 486. Nucl. Acids Res. vol. 24 pp. 1404–1411, 1996.
Anton et al., *J. Virol.*, 69, 4600–4606 (1995).
Argos et al., *EMBO J.*, 5, 433–440 (1994).
Barinaga, *Science*, 265, 26, 28 (1994).
Baubonis et al., *Nucleic Acids Research*, 21, 9, 2025–2029 (1993).
Brunelli et al., *Yeast*, 9, 1309–1318 (1993).
Clontech (Palo Alto, CA) 1995/1996 Catalog, 187–188.
Fiering et al., *Proc. Natl. Acad. Sci.*, 90, 8469–8473 (1973).
Fukushige et al., *Proc. Natl. Acad. Sci.*, 89, 7905–7909 (1992).
Gage et al., *J. Virol.*, 66, 5509–5515 (1992).
Gu et al., *Cell*, 73, 1155–1164 (1993).
Hasan et al., *Gene*, 150, 51–56 (1994).
Hoess et al., *Nucleic Acids Research*, 14, 2287–2300 (1986).
Holt et al., *Gene*, 133, 95–97 (1993).
InVitrogen (San Diego, CA) 1995 Catalog, 35.
Jalanko et al., *Arch. Virol.*, 103, 157–166 (1988).
Jalanko et al., *Biochemica et Biophysica Acta*, 949, 206–212 (1988).
Jayaram, *TIBS*, 19, 78–82 (1994).
Jung et al., *Science*, 259, 984–987 (1993).
Kanegae et al., *Nucleic Acids Research*, 23, 3816–3821 (1995).
Kilby et al., *TIG*, 9, 413–421 (1993).
Kioussis et al., *EMBO J.*, 6, 355–361 (1987).
Kirchmaier et al., *J. Virol.*, 69, 1280–1283 (1995).
Kotin et al., *Human Gene Therapy*, 5, 793–801 (1994).
Lakso et al., *Proc. Natl. Acad. Sci.*, 89, 6232–6236 (1992).
Landy, *Current Opinion in Genetics and Development*, 3, 699–707 (1993).
Levitskaya et al., *Nature*, 375, 685–688 (1995).
Lupton et al., *Mol. Cell. Biol.*, 5, 2533–2542 (1985).
Metzger et al., *Pro. Natl. Acad. Sci.*, 92, 6991–6995 (1995).
Middleton et al., *Advances in Virus Research*, 40, 19–55 (1991).
Morris et al., *Nucleic Acids Res.*, 19, 5895–5900 (1991).
Muzyczka et al., *Current Topics in Microbiol. and Immunol.*, 158, 97–129 (1992).
O'Gorman et al., *Science*, 251, 1351–1355 (1991).
Odell et al., *Plant Physiol.*, 106, 447–458 (1994).
Orban et al., *Proc. Natl. Acad. Sci.*, 89, 6861–6865 (1992).
Peakman et al., *Nucleic Acids Res.*, 20, 495–500 (1992).
Reisman et al., *Mol. Cell. Biol.*, 5, 1822–1832 (1985).
Rossant et al., *Nature Medicine*, 1, 592–594 (1995).
Sauer et al., *Proc. Natl. Acad. Sci.*, 84, 9108–9112 (1987).
Sauer et al., *Gene*, 70, 331–341 (1988).
Sauer et al., *Proc. Natl. Acad. Sci.*, 85, 5166–5170 (1988).
Sauer et al., *Nucleic Acids Res.*, 17, 147–161 (1989).
Sauer et al., *J. Mol. Biol.*, 223, 911–928 (1992).
Sauer et al., *Methods*, 4, 143–149 (1992).
Sauer, *Methods in Enzymol.*, 225, 890–900 (1993).
Shelling et al., *Gene Therapy*, 165–169 (1994).
Sugden et al., *J. Virol.*, 63, 2644–2649 (1989).
Thrasher et al., *Gene Therapy*, 2, 481–485 (1995).
Watson et al., *In Molecular Biology of Gene* (Fourth Edition), 639–640 (Benjamin/Cimmings Publishing Co., Inc. 1987).
Yates et al., *Nature*, 313, 812–815 (1985).
Yates et al., *Proc. Natl. Acad. Sci.*, 81, 3806–3810 (1984).
Young et al., *Gene*, 62, 171–185 (1988).

*Primary Examiner*—John S. Brusca
*Attorney, Agent, or Firm*—Leydig, Voit & Mayer, Ltd.

[57] ABSTRACT

The present invention provides methods for site-specific recombination in a cell, as well as vectors which can be employed in such methods. The methods and vectors of the present invention can be used to obtain persistent gene expression in a cell and to modulate gene expression.

One preferred method according to the invention comprises contacting a cell with a vector comprising an origin of replication functional in mammalian cells located between first and second recombining sites located in parallel. Another preferred method comprises, in part, contacting a cell with a vector comprising first and second recombining sites in antiparallel orientations such that the vector is internalized by the cell. In both methods, the cell is further provided with a site-specific recombinase that effects recombination between the first and second recombining sites of the vector.

62 Claims, 15 Drawing Sheets

METHODS AND VECTORS FOR SITE-SPECIFIC RECOMBINATION

This application is a continuation of PCT/US96/14123, which was filed on Aug. 27, 1996, as a continuation-in-part of U.S. patent application Ser. No. 08/522,684, which was filed on Sep. 1, 1995, and issued on Sep. 1, 1998, as U.S. Pat. No. 5,801,030.

TECHNICAL FIELD OF THE INVENTION

The present invention relates to methods for site-specific recombination in a cell, as well as vectors which can be employed in such methods. The methods and vectors of the present invention can be used to obtain persistent gene expression in a cell and to modulate gene expression.

BACKGROUND OF THE INVENTION

The past few years have heralded a sharp increase in the availability of new approaches to gene therapy, and the number of diseases that appear potentially amenable to treatment using so-called "therapeutic genes". Generally, a therapeutic gene is a gene that corrects or compensates for an underlying protein deficit or, alternately, that is capable of down-regulating a particular gene, or counteracting the negative effects of its encoded product, in a given disease state or syndrome. Moreover, a therapeutic gene can be a gene that mediates cell killing, for instance, in the gene therapy of cancer. A successful therapeutic outcome using gene therapy hinges on the appropriate expression of the therapeutic gene, and potentially its long-term persistence in the host. Whereas expression can typically be effectively controlled using various cloning strategies that are well known to those skilled in the art, persistence (i.e., the long-term expression of the gene in the host cell) has proven more elusive.

As a general approach toward obtaining prolonged gene expression, researchers employ as a vehicle for transfer of the therapeutic gene a vector which demonstrates longevity in the host. Stability is maximized with use of a vector that integrates into the genome of the host, allowing for simultaneous integration of the therapeutic gene carried by the vector. Along these lines, retrovirus, which as part of its life cycle integrates into the host genome, has proven a useful tool. However, the use of retrovirus is not without its attendant problems. For instance, stable integration of a retroviral vector is confined to target cells that are actively synthesizing DNA; its carrying capacity is limited due to the relatively small size of the vector; the vector exhibits a lack of tissue tropism; and such a vector is rapidly inactivated by antibodies when given systemically. As a consequence of these and other shortcomings which accompany the use of a retrovirus, many researchers have turned to adenovirus (Ad) as an alternate vector for gene therapy (see, e.g., Rosenfeld et al., *Science*, 252, 431–434 (1991); Rosenfeld et al., *Cell*, 68, 143–155 (1992)).

Ads are nonenveloped, regular icosahedrons, 65–80 nanometers in diameter, that consist of an external capsid and an internal core (Ginsberg (ed.), The Adenoviruses, Plenum Press, NY (1984)). The Ad core contains a linear, double-stranded DNA molecule. Two human serotypes, namely Ad2 and Ad5, have been studied intensively and have provided the bulk of available information about Ads. This information, as well as the various useful properties of Ad (among other things, replication-deficient recombinant viruses are easily made and produced in large quantities using complementing cell lines, Ad is capable of infecting almost all cell types including terminally differentiated or non-proliferative cells, and no malignancies have been associated with Ad infection) have enabled the exploitation of Ad as an efficient gene delivery vector both in vivo and in vitro (see, e.g., Rosenfeld et al. (1991), supra; Rosenfeld et al. (1992), supra; Engelhardt et al., *Hum. Gene Ther.*, 4, 79–769 (1993); Crystal et al., *Nat. Genet.*, 8, 42–51 (1994); Lemarchand et al., *Circ. Res.*, 72, 1132–1138 (1993); Guzman et al., *Circ. Res.*, 73, 1202–1207 (1993); Bajocchi et al., *Nat. Genet.*, 3, 229–234 (1993); Mastrangeli et al., *J. Clin. Invest*, 91, 225–234 (1993)).

Despite these advantages of Ad vectors, the long-term expression of an administered therapeutic gene has not satisfactorily been obtained using Ad as a gene transfer vehicle. First generation Ad vectors deleted the essential E1 region of the virus (Rosenfeld et al. (1992), supra; Boucher et al., *Hum. Gene Ther.*, 5, 615–39 (1994)). Trans gene product from these viral vectors is detected for approximately two weeks in the rodent model system before returning to background levels. In comparison, in immune-suppressed mice, the length of the period during which gene expression can be detected following infection is substantially increased, as is the level of expression (Yang et al., *J. Virol.*, 69, 2004–15 (1995); Yang et al., *Proc. Natl. Acad. Sci.*, 10, 4407–11 (1994)). These data suggest that immune surveillance is responsible for the relatively poor performance of the first generation Ad vectors. Moreover, the inability of Ad to be maintained in a cell integrated into the host cell genome means that cells which express the therapeutic gene encoded by the vector are ultimately lost from the cell.

Accordingly, many researchers working with Ad have sought alternative means of stabilizing recombinant vectors such that long-lived gene expression can be obtained. One such means that has proven effective in other systems is that of maintaining the integrity of the transferred gene in the host in the form of an episome. An episome is an extrachromosomal genetic element that replicates independently of the host cell genome. To this end, the capability of Epstein-Barr virus (EBV) to form an episome in its latent state has been usurped by researchers as a means to generate episomes from various double-stranded DNA templates.

EBV is a human lymphotropic herpes virus which causes infectious mononucleosis and is associated with at least two human cancers (Reisman et al., *Molec. Cell. Biol.*, 5, 1822–1832 (1985)). EBV contains two origins of replication, oriLyt and oriP. During latency, EBV exists as a closed circular double-stranded DNA molecule which employs oriP in its replication, and which is maintained at a copy number ranging from 10 to 200 per cell (Young et al., *Gene*, 62, 171–185 (1988)). Plasmids that harbor oriP can be maintained in cells that also express the nuclear antigen EBNA-1 (see, e.g., Yates et al., *Nature*, 313, 812–815 (1985); Jalanko et al., *Biochemica et Biophysica Acta*, 949, 206–212 (1988); Kioussis et al., *EMBO J.*, 6, 355–361 (1987); Jalanko et al., *Arch. Virol.*, 103, 157–166 (1988); Sugden et al., *J. Virol.* 63, 2644–2649 (1989)). In the presence of EBNA-1, oriP permits plasmid replication in a variety of mammalian cells that EBV is incapable of infecting in culture (Reisman et al., supra; Yates et al., *Proc. Natl. Acad Sci.*, 81, 3806–3810 (1984)). The oriP origin contains two cis-acting elements that are required for its activity (reviewed in Middleton et al., *Advances in Virus Research*, 40, 19–55 (1991)). The elements are separated by 1,000 base pairs (bp), and both are composed of multiple degenerate copies of a 30 bp segment. The first element, termed the family of repeats, or FR, contains 20 tandem 30 bp repeats.

The second element is comprised of a 114 bp segment that contains a 65 bp dyad symmetry element, or DS.

Mutagenesis studies reveal that the two regions of oriP function vis-a-vis each other in an orientation- and distance-independent manner (Middleton et al., supra). Deletion of the intervening spacer region, or addition to this region of more than 1,000 bp, does not affect the function of oriP. The FR element is known to function as an enhancer, but its role in replication remains unclear. Moreover, the 20 tandem repeats comprising FR can be replaced by multiple copies of DS. As few as eight of the 20 tandem repeats found in the FR enhancer are sufficient in short term assays for both enhancer activity and plasmid replication.

EBNA-1 binds to the 30 bp repeats present in both elements of oriP. The EBNA-1 protein is required for the initiation of DNA replication near DS which occurs once per cycle during the S phase of the EBV cell cycle (Middleton et, al., supra). A glycine-alanine repetitive sequence which comprises approximately ⅓ of the protein and a small region in the carboxyl terminus of the protein is dispensable for plasmid replication (Yates et al. (1985), supra; Lupton et al., Mol. Cell. Biol., 5, 2533–2542 (1985)). However, this sequence prevents the immune system from detecting EBNA-1 and, consequently, would appear necessary for persistence of EBV and EBV-derived vectors (Levitskaya et al., Nature, 375, 685–688 (1995)).

The stability of episomes obtained using EBV is potentially limiting for long-term persistence and expression of a therapeutic gene inasmuch as there is at least some possibility of an error in partitioning newly synthesized episomes between daughter cells, and in view of the pervasive negative selection pressure with respect to extrachromosomal genetic elements. Integration of the episome into a nondeleterious locus in the genome, i.e., a safe haven for the transferred gene, would obviate this potential lack of stability. Along these lines, adeno-associated virus (AAV) demonstrates a unique ability to integrate with high frequency into human chromosome 19q13.3-qter (Kotin et al., Human Gene Therapy, 5, 793–801 (1994)). This ability of AAV to integrate into a defined and benign genomic site eliminates the risk of insertional mutagenesis due to inadvertent gene activation or inactivation that accompanies random insertion of DNA (Shelling et al., Gene Therapy, 165–169 (1994)).

In terms of its general features, AAV is a human parvovirus that can be propagated either as an integrated provirus, or by lytic infection (Muzyczka, Current Topics in Microbiol. and Immunol., 158, 97–129 (1992)), and which has been employed as a vector for eukaryotic cells (see,. e.g., U.S. Pat. Nos. 4,797,368 and 5,173,414; Tratschin et al., Mol. Cell. Biol., 4, 2072–2081 (1984); GenBank Database Accession Number J01901 or AA2C). The lytic phase of AAV infection requires the expression of the Ad early gene products E1a, E1b, E2a, E4, and VA RNA (Kotin et al., supra). Latent infections are established by infection of AAV in the absence of helper virus. Under these circumstances, AAV efficiently integrates into the cellular genome, and is maintained in that state unless challenged with Ad.

Only two components of AAV are required for locus-directed integration of a foreign gene into the human genome: the Rep proteins, and the AAV inverted terminal repeats (ITRs). The four Rep proteins are each encoded by the same gene, and are generated by alternative splicing of nascent mRNAs (Kyöstiö et al., J. Virol., 68, 2947–2957 (1994)). The two larger Rep proteins, Rep78 and Rep68, bind the AAV ITRs and act as ATP-dependent, sequence-specific endonucleases with helicase activity to unwind the region of the ITRs during AAV DNA replication (Hölscher et al., J. Virol., 68, 7169–7177 (1994)). The smaller Rep proteins, Rep52 and Rep40, appear essential for the accumulation of single-stranded progeny genomes used in packaging the virus.

The AAV ITRs are located at each end of the genome. When the viral ITRs are single-stranded, they form T-shaped hairpin structures (Snyder et al., J. Virol., 67, 6096–6104 (1993)). The origin of replication, packaging, integration and excision signals are also found located within the region of the viral ITRs. Binding of Rep proteins to the AAV ITRs is consistent with the essential role of this region in ITR-dependent replication and locus-directed integration. In the absence of Rep proteins, replication does not occur, and integration into the genome appears to be a random event (Kotin et al., supra). The ITRs can function either in their native state or as cloned into a plasmid as double-stranded DNA. With appropriate application of Rep proteins (e.g., by providing Rep proteins through coding sequences located in trans), foreign sequences incorporated between the ITRs can be excised from a plasmid, replicated and integrated into the host cell genome.

The implementation of the EBV strategy to generate an episome, or the AAV strategy to stabilize an episome or sequences carried by the episome through incorporation into a host cell genome, requires tight regulation of the relevant regulatory protein in each system (e.g., EBNA-1 for EBV, and Rep proteins for AAV). One approach that has been employed by researchers for achieving tight regulation of gene expression is to control expression of a gene or genetic sequence via a site-directed recombination event. Two well studied systems that allow site-specific recombination and have been used in a variety of applications are the phage P1 Cre/Lox system and the yeast Flp/Frt system.

The Cre and Flp proteins belong to the $\lambda$ integrase family of DNA recombinases (reviewed in Kilby et al., TIG, 9, 413–421 (1993); Landy, Current Opinion in Genetics and Development, 3, 699–707 (1993); Argos et al., EMBO J., 5, 433–440 (1986)). The Cre and Flp recombinases show striking similarities, both in terms of the types of reactions they carry out and in the structure of their target sites and mechanism of recombination (see, e.g., Jayaram, TIBS, 19, 78–82 (1994); Lee et al., J. Biolog. Chem., 270, 4042–4052 (1995); Whang et al., Molec. Cell. Biolog., 14, 7492–7498 (1994); Lee et al., EMBO J., 13, 5346–5354 (1994); Abremski et al., J. Mol. Biol., 192, 17–26 (1986); Adams et al., J. Mol. Biol., 226, 661–673 (1992)). For instance, the recombination event is independent of replication and exogenous energy sources such as ATP, and functions on both supercoiled and linear DNA templates.

The Cre and Flp recombinases exert their effects by promoting recombination between two of their target recombination sites, Lox and Frt, respectively. Both target sites are comprised of inverted palindromes separated by an asymmetric sequence (see, e.g., Mack et al., Nucleic Acids Research, 20, 4451–4455 (1992); Hoess et al., Nucleic Acids Research, 14, 2287–2300 (1986); Kilby et al., supra). The asymmetry provides directionality to the recombination event. Namely, recombination between target sites arranged in parallel (i.e., so-called "direct repeats") on the same linear DNA molecule results in excision of the intervening DNA sequence as a circular molecule (Kilby et al., supra). Recombination between direct repeats on a circular DNA molecule excises the intervening DNA and generates two circular molecules. In comparison, recombination between antiparallel sites (i.e., sites which are in opposite orientation, or so-called "inverted repeats") on a linear or circular DNA molecule results in inversion of the internal sequence. Even though recombinase action can result in reciprocal exchange of regions distal to the target site when targets are present on separate linear molecules, intramolecular recombination is favored over intermolecular recombination.

Both the Cre/Lox and Flp/Frt recombination systems have been used for a wide array of purposes. For instance, site-specific integration into plant, insect, bacterial, yeast and mammalian chromosomes has been reported (see, e.g., Sauer et al., *Proc. Natl. Acad. Sci.,* 85, 5166–5170 (1988); Fukushige et al., *Proc. Natl. Acad. Sci.,* 89, 7905–7907 (1992); Baubonis et al., *Nucleic Acids Research,* 21, 2025–2029 (1993); Hasan et al., *Gene,* 150, 51–56 (1994); Golic et al., *Cell,* 59, 499–509 (1989); Sauer, *Mol. Cell. Biolog.,* 7, 2087–2096 (1987); Sauer et al., *Methods: Companion to Methods in Enzymol.,* 4, 143–149 (1992); Sauer et al., *The New Biologist,* 2, 441–449 (1990); Sauer et al., *Nucleic Acids Res.,* 17, 147–161 (1989); Qin et al., *Proc. Natl. Acad. Sci.,* 91, 1706–1710 (1994); Orban et al., *Proc. Natl. Acad. Sci.,* 89, 6861–6865 (1992)). Eukaryotic viral vectors have been assembled, and inserted DNA has been recovered, using these systems (see, e.g., Sauer et al., *Proc. Natl. Acad. Sci.,* 84, 9108–9112 (1987); Gage et al., *J. Virol.,* 66, 5509–5515 (1992); Holt et al., *Gene,* 133, 95–97 (1993); Peakman et al., *Nucleic Acids Res.,* 20, 495–500 (1992)). Specific deletions of chromosomal sequences and rearrangements have also been engineered, and excision of foreign DNA as a plasmid from λ vectors is presently possible (see, e.g., Barinaga, *Science,* 265, 27–28 (1994); Rossant et al., *Nature Medicine,* 1, 592–594 (1995); Sauer, *Methods in Enzymol.,* 225, 890–900 (1993); Sauer et al., *Gene,* 70, 331–341 (1988); Brunelli et al., *Yeast,* 9, 1309–1318 (1993); InVitrogen (San Diego, Calif.) 1995 Catalog, 35; Clontech (Palo Alto, Calif.) 1995/1996 Catalog, 187–188). Cloning schemes have been generated so that recombination either reconstitutes or inactivates a functional transcription unit by either deletion or inversion of sequences between recombination sites (see, e.g., Odell et al., *Plant Physiol.,* 106, 447–458 (1994); Gu et al., *Cell,* 73, 1155–1164 (1993); Lakso et al., *Proc. Natl. Acad. Sci.,* 89, 6232–6236 (1992); Fiering et al., *Proc. Natl. Acad. Sci.,* 90, 8469–8473 (1973); O'Gorman et al., *Science,* 251, 1351–55 (1991); Jung et al., *Science,* 259, 984–987 (1993)). Similarly, positive and negative strategies for selecting or screening recombinants have been developed (see, e.g., Sauer et al., *J. Mol. Biol.,* 223, 911–928 (1992)). The genes encoding the Cre or Flp recombinases have been provided in trans under the control of either constitutive, inducible or developmentally-regulated promoters, or purified recombinase has been introduced (see, e.g., Baubonis et al., supra; Dang et al., *Develop. Genet.,* 13, 367–375 (1992); Chou et al., *Genetics,* 131, 643–653 (1992); Morris et al., *Nucleic Acids Res.,* 19, 5895–5900 (1991)). The use of the recombinant systems or components thereof in transgenic mice, plants and insects among others reveals that hosts express the recombinase genes with no apparent deleterious effects, thus confirming that the proteins are generally well-tolerated (see, e.g., Orbin et al., *Proc. Natl. Acad. Sci.,* 89, 6861–6865 (1992)).

More recently, researchers have employed replication-deficient Ad vectors containing the phage P1 gene for Cre as a means of studying intracellular Cre-mediated recombination (Anton et al., *J. Virol.,* 69, 4600–4606 (1995)). In these experiments, the Cre-expressing Ad vector was supplied to cells along with another Ad vector, in which the coding sequence of a reporter gene was separated from any promoter by an extraneous spacer sequence flanked by parallel Lox sites. Cre-mediated recombination resulted in excision of the spacer sequence, and a turning on of the formerly silent reporter gene. This approach would appear to allow for only the positive modulation of gene expression, and not stable gene expression, inasmuch as the gene switched on by the recombination event will be expressed only as long as the replication-deficient Ad vector is maintained in the host cell. Moreover, there is a possibility of the reverse recombination reaction simultaneously switching off the reporter gene and imposing an upper limit on the expression level to be obtained, due to continuing production of Cre within the host cell (Anton et al., supra, page 4605).

Accordingly, there remains a need for expression systems in which the potential of Ad and other gene therapy vectors can be more fully realized. The present invention seeks to provide such expression systems. In particular, it is an object of the present invention to provide methods for site-specific recombination in a cell, and vectors which can be employed in such methods, which allow prolonged gene expression as well as modulation of gene expression, and which overcome some of the aforementioned problems inherent in prior gene expression systems. These and other objects and advantages of the present invention, and additional inventive features, will be apparent from the description of the invention provided herein.

BRIEF SUMMARY OF THE INVENTION

The present invention relates to methods for site-specific recombination in a cell, as well as vectors which can be employed in such methods. The methods and vectors of the present invention can be used to obtain persistent gene expression in a cell and to modulate gene expression.

More specifically, one preferred method according to the invention comprises the steps of: (a) contacting a cell with a vector comprising an origin of replication functional in mammalian cells located between first and second recombining sites located in parallel, such that the vector is internalized by the cell, and (b) providing the cell with a site-specific recombinase that effects recombination between the first and second recombining sites of the vector.

Another preferred method according to the invention comprises, in part, the steps of: (a) contacting a cell with a vector comprising first and second recombining sites in antiparallel orientations such that the vector is internalized by the cell, and (b) providing the cell with a site-specific recombinase that effects recombination between the first and second recombining sites of the vector.

DETAILED DESCRIPTION OF THE INVENTION

Figure 1A:
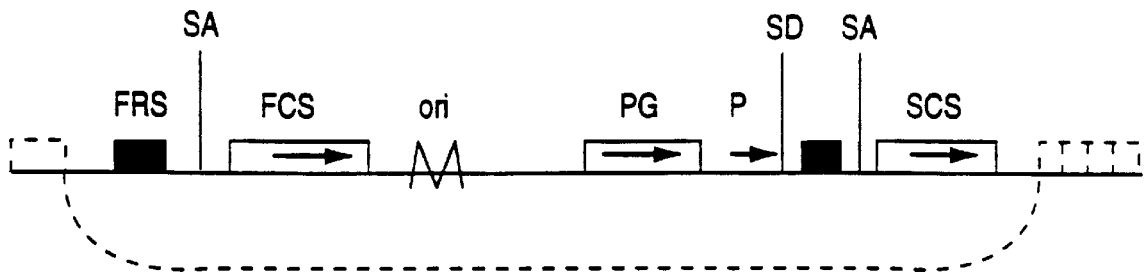
FIGS. 1A–1C are schematic diagrams depicting a vector with parallel recombining sites useful in the context of the present invention before delivery to the host cell (FIG. 1A) and the truncated virus or circular structure (FIG. 1B) and episome (FIG. 1C) resulting from the intracellular recombination event which occurs after delivery of the vector to the host cell in accordance with the invention. Either a closed-circular vector (i.e., flanking plasmid or viral sequences indicated by the stippled line) or a linear vector (i.e., flanking viral sequences indicated by the stippled boxes) can be employed for delivery of the episome to the host cell. The region between and including FRS to SCS can be in either orientation with respect to the flanking vector sequences. The arrows indicate the direction of transcription. Abbreviations: RS, recombining site; FRS, first recombining site; SRS, second recombining site; SA, splice acceptor site; SD, splice donor site; FCS, first coding sequence; SCS, second coding sequence; P, promoter; PG, passenger gene; ori, origin of replication.

The present invention provides methods for obtaining persistent expression of a gene in a host cell and vectors which can be employed in such methods. The methods and vectors can also be employed to modulate gene expression. The methods and vectors according to this invention couple in a novel fashion (1) the unique capabilities EBV and AAV (i.e., the ability of EBV to generate episomes, and the ability of AAV to integrate into the human genome), (2) the recombinase activities of recombination systems such as the Cre/Lox and Flp/Frt recombination systems, and (3) various desirable properties of Ad, and other similar viral and plasmid vectors.

Definitions

For ease of reference, the abbreviations and designations used herein to describe the present inventive methods and vectors are set forth in Table 1.

TABLE 1

| Abbreviations and Designations | |
|---|---|
| AAV | Adeno-associated virus |
| Ad | Adenovirus |
| bp | Base pairs |
| cDNA | Complementary DNA |
| CMV | Cytomegalovirus |
| Cre | Phage P1 site-specific recombinase |
| DNA | Deoxyribonucleic acid |
| DS | Dyad symmetry element comprising one element of oriP |
| EBV | Epstein-Barr virus |
| EBNA-1 | Protein which binds oriP and modulates replication of EBV and EBV-derived episomes |
| FCS | First coding sequence |
| Flp | Target site recognized by the yeast Frt protein |
| FR | EBV family of repeats comprising one element of oriP |
| FRS | First recombining site |
| Frt | Yeast site-specific recombinase |
| HSV | Herpes simplex virus types I and II |
| ITR | AAV inverted terminal repeats that contain sequences that function as an origin of replication |
| kb | kilobase pairs |
| Lox | Target site recognized by the phage P1 Cre protein |
| oriLyt | EBV origin of repiication involved in replication in the lytic phase |
| oriP | EBV origin of replication involved in replication in the latent state |
| P | Promoter |
| PCR | Polymerase chain reaction |
| PG | Passenger gene |
| Rep | Proteins which bind the ITRs that act in replication and integration into the genome of AAV and AAV-derived vectors |
| RNA | Ribonucleic acid |
| RS | Recombining site |
| RSV | Rous sarcoma virus |
| SA | Splice acceptor site |
| SCS | Second coding sequence |
| SD | Splice donor site |
| SRS | Second recombining site |
| SV40 | Simian virus 40 |

Also, according to the invention and as further defined herein, a "vector" is a molecule (e.g., virus or plasmid) that serves to transfer coding information to a host cell. An "origin of replication" is a sequence on a vector or host cell chromosome that renders extragenomic elements (e.g., viruses or plasmids) capable of replicating independently of the host cell genome.

A "gene" is any nucleic acid sequence coding for a protein or a nascent RNA molecule. A "passenger gene" is any gene which is not typically present in and is subcloned into a vector according to the present invention, and which upon introduction into a host cell is accompanied by a discernible change in the intracellular environment (e.g., by an increased level of deoxyribonucleic acid (DNA), ribonucleic acid (RNA), peptide, or protein, or by an altered rate of production or degradation thereof). A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. Whereas a gene comprises coding sequences plus any non-coding sequences, a "coding sequence" does not include any non-coding (e.g., regulatory) DNA. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and may be provided in the form of either DNA or cDNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region.

According to this invention, "recombining sites" are comprised of inverted palindromes separated by an asymmetric sequence at which a site-specific recombination reaction can occur. The present invention describes preferred embodiments wherein recombining sites (e.g., first and/or second recombining sites) preferably are employed. However, more or less recombining sites (e.g., 1, or a multiplicity of sites, such as, for instance, 3, 4, 5, or 6 recombining sites) also can be employed. Moreover, different types of recombining sites can be used, e.g., a combination of two Lox sites with two Flp sites. A "recombinase" is a protein which carries out recombination between particular recombining sites.

Also according to the invention, a coding sequence is "operably linked" to a promoter when the promoter is capable of directing transcription of that coding sequence. A promoter "adjoins" a recombining site (i.e., a first or second recombining site) when the promoter is capable of exerting its effect on transcription through the region of the recombining site and upon sequences linked to the recombining site. A coding sequence (i.e., a coding sequence or a second coding sequence) "adjoins" a recombining site (i.e., a first or second recombining site) when the coding sequence is at such a distance from the recombining site that it can be transcriptionally controlled by a promoter linked to the recombining site which exerts its effect through the region of the recombining site and upon the coding sequence. For this to occur, preferably the coding sequence is located within about 1000 bp of the recombining site, and even more preferably the coding sequence is located within about 500 bp of the recombining site. However, in cases where the promoter is separated from the coding sequence it controls by an oppositely-oriented intervening coding sequence, preferably the distance between the promoter and coding sequence it controls is about 5000 bp or less, more preferably, about 2000 bp or less. A "polycistronic message" is a single mRNA from which more than one peptide or protein is translated, as described further herein.

Methods for Site-Directed Recombination

The present invention provides two methods to effect site-specific recombination in a cell. Both recombination methods involve contacting a cell with a vector comprising first and second recombining sites such that the vector is internalized by the cell, and then providing the cell with a site-specific recombinase that effects recombination between the first and second recombining sites of the vector. The first site-specific recombination method involves the use of a vector (i.e., a "parallel recombination vector") comprising first and second recombining sites located in a parallel orientation, whereas the second site-specific recombination method involves the use of a vector (i.e., an "antiparallel recombination vector") comprising the first and second recombining sites located in an antiparallel (or opposite) orientation.

The parallel recombination method is capable of effecting site-specific recombination in a cell such that the recombination event generates an episome comprising an origin of replication capable of functioning in mammalian cells, which can replicate autonomously of the host genome and can be employed to impart stable maintenance in host cells upon vectors carrying one or more passenger genes. The parallel recombination method is useful in that it can be employed to stabilize vectors which typically do not integrate into the host cell genome (e.g., Ad or HSV vectors) by imparting to such vectors an ability to replicate via a "lysogenic-like" pathway. Thus, the method can be employed to obtain stable gene expression by stabilizing vectors carrying one or more passenger genes.

The parallel recombination method also can be employed to effect site-specific recombination in a cell such that the recombination event generates a so-called "miniplasmid", which does not comprise an origin of replication that is capable of functioning in mammalian cells, and which is not capable of replicating autonomously of the host genome. Notably, the second recombination product generated by the parallel recombination event (i.e., the product other than the episome or miniplasmid, which itself comprises either a linear or a closed-circular structure depending on whether the original substrate for the recombination reaction is, respectively, either linear or closed-circular) also may be functional in the cell. Such a miniplasmid, as further described herein, can prove of use for the short-term delivery of proteins (e.g., Rep protein) to cells.

Alternately, it also is possible that the vector employed for site-specific recombination comprises more than one origin of replication prior to the recombination event. Vectors that comprise more than one replication origin are known in the art.

As described further herein, both the parallel and antiparallel recombination methods can be employed to either upor down-regulate transcription of a coding sequence, or to simultaneously up-regulate transcription of one coding sequence and down-regulate transcription of another, through the recombination event. The antiparallel recombination method differs from the parallel recombination method in that it does not involve the formation of an episome or miniplasmid.

The recombination methods according to the invention are in a cell, which preferably is a eukaryotic cell. A eukaryotic cell is a cell which possesses a true nucleus surrounded by a nuclear membrane. Preferably the eukaryotic cell is of a multicellular species (e.g., as opposed to a unicellular yeast cell), and even more preferably is a mammalian (optimally human) cell. However, the methods also can be effectively carried out using a wide variety of different cell types such as avian and fish cells, and mammalian cells including but not limited to rodent, ape, chimpanzee, feline, canine, ungulate (such as ruminant or swine), as well as human cells. Moreover, if vector transfer to a particular cell type is limited due, for instance, to a lack of receptors for a particular virus such as adenovirus, transfer can be increased using methods employed, for example, to carry human adenovirus into blood or other cell types. For instance, the virus can be coupled to a DNA-polylysine complex containing a ligand (e.g., transferrin) for mammalian cells (Wagner et al., *Proc. Natl. Acad. Sci.*, 89, 6099–6103 (1992)), or by using other similar methods which are known to those skilled in the art.

Any suitable vector can be utilized in the present inventive methods, particularly the novel vectors described herein. Thus, the vector utilized in accordance with the present inventive methods can encompass any vector, linear or circular, that is appropriate for introduction of nucleic acids into eukaryotic cells, and is capable of functioning as a vector as that term is understood by those of ordinary skill in the art, so long as the vector is predominantly comprised of double-stranded DNA during some phase of its existence. Preferably, the resultant vector is compatible with the host cell, i.e., is capable of transcribing the nucleic acid sequences subcloned in the vector, and if desired, also is capable of translating the nascent mRNA.

The vector optimally is of viral origin, and can contain one or more heterologous or recombinant sequences, e.g., a coding sequence, a passenger gene, promoter, or the like. Preferably the vector contains the minimal sequences required for packaging and delivery to the cell. The vector desirably is comprised, in part, of a virus that is either enveloped or nonenveloped. For instance, preferably a vector is a nonenveloped virus from the family Hepadnaviridae, Parvoviridae, Papovaviridae, or Adenoviridae. A preferred nonenveloped virus according to the invention is a virus of the family Hepadnaviridae, especially of the genus Hepadnavirus. A virus of the family Parvoviridae desirably is of the genus Parvovirus (e.g., parvoviruses of mammals and birds) or Dependovirus (e.g., adeno-associated viruses (AAVs)). A virus of the family Papovaviridae preferably is of the subfamily Papillomavirinae (e.g., the papillomaviruses including, but not limited to, human papillomaviruses (HPV) 1–48 and bovine papillomaviruses (BPV)) or the subfamily Polyomavirinae (e.g., the polyomaviruses including, but not limited to, JC, SV40, BK virus, and mouse polyomavirus). A virus of the family Adenoviridae desirably is of the genus Mastadenovirus (e.g., mammalian adenoviruses) or Aviadenovirus (e.g., avian adenoviruses). Similarly, a vector can be an enveloped virus from the family Hexpesviridae, or can be a Sindbis virus. A preferred enveloped virus according to the invention is a virus of the family Herpesviridae, especially of the subfamily Alphahezpesvirinae (e.g., the herpes simplex-like viruses), genus Simplexvirus (e.g., herpes simplex-like viruses), genus Varicellavirus (e.g., varicella and pseudorabies-like viruses), subfamily Betaherpesvirinae (e.g., the cytomegaloviruses), genus Cytomegalovirus (e.g., the human cytomegaloviruses), subfamily Gammaherpesvirinae (e.g., the lymphocyte-associated viruses), or genus Lymphocryptovirus (e.g., EB-like viruses). In particular, preferably the virus component of the vector is selected from the group consisting of Ad, herpes simplex virus types I and II (HSV), EBV, vaccinia virus, papilloma virus (e.g., either human (HPV) or bovine (BPV)), JC, simian virus 40 (SV40), polyomavirus (e.g., either human or mouse), hepatitis virus B, and cytomegalovirus (CMV). Moreover, for practice of the parallel recombination method wherein an episome desirably is formed, preferably, the vector is comprised, in part, of vectors derived from viruses which do not form proviruses as part of their replicative cycle.

An especially preferred vector according to the invention is an adenoviral vector (i.e., a viral vector of the family Adenoviridae, optimally of the genus Mastadenovirus). The adenovirus is of any serotype vector. Adenoviral stocks that can be employed as a source of adenovirus can be amplified from the adenovirus serotypes from type 1 through 47 currently available from American Type Culture Collection (ATCC, Rockville, Md.), or from any other serotype of adenovirus available from any other source. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22–30, 32, 33, 36–39, 42–47), subgroup E (serotype 4), subgroup F (serotype 40, 41), or any other adenoviral serotype. Preferably, however, an adenovirus is an Ad2 or Ad5 serotype.

The Ad employed for nucleic acid transfer can be wild-type (i.e., replication-competent). Alternately, the Ad can comprise genetic material with at least one modification therein, which can render the virus replication-deficient. The modification to the Ad genome can include, but is not limited to, addition of a DNA segment, rearrangement of a DNA segment, deletion of a DNA segment, replacement of a DNA segment, or introduction of a DNA lesion. A DNA segment can be as small as one nucleotide and as large as 36 kilobase pairs (kb) (i.e., the approximate size of the Ad genome) or, alternately, can equal the maximum amount which can be packaged into an Ad virion (i.e., about 38 kb). Preferred modifications to the Ad genome include modifications in the E1, E2, E3 or E4 region.

In the methods and vectors of the present invention, the vectors may further comprise a passenger gene. The passenger gene can be in any orientation in the vector. Any suitable passenger gene can be employed, such as a reporter gene or a therapeutic gene, so long as the passenger gene is capable of being expressed in a cell in which the vector has been internalized. For instance, the gene can comprise a reporter gene, or a nucleic acid sequence which encodes a protein that can in some fashion be detected in a cell. The gene also can comprise a therapeutic gene which exerts its effect at the level of RNA or protein. For instance, the protein can be employed in the treatment of an inherited disease, such as, e.g., the cystic fibrosis transmembrane conductance regulator cDNA for the treatment of cystic fibrosis. The protein encoded by the therapeutic gene may exert its therapeutic effect by resulting in cell killing. For instance, expression of the gene in itself may lead to cell killing, as with expression of the diphtheria toxin A gene, or the expression of the gene, may render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-β-D-arabinofuranosil)-5-iodouracil). This cell killing approach to gene therapy (which may, for instance, be employed in the treatment of cancer) can further be enhanced with use in the vector of a so-called "runaway replication origin" as described further herein. However, the use of such a runaway replication system is not limited to cell killing, and can be employed, for instance, under circumstances wherein a transient high level of expression is desired (e.g., for a "bolus-type" delivery of a protein by recombinant means).

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Such a passenger gene can encode any other protein, for instance, EBNA-1, and can be present alone or in addition to further passenger gene(s) located between the first and second recombining sites.

The passenger gene being transferred can comprise DNA which can be as small as one repeat unit (i.e., a nucleotide for DNA) and as large as reasonably can be isolated or synthesized, or transferred to a host cell using the methods of the present invention, and considering packaging constraints of viral vectors, or upper size limits of plasmid vectors. The passenger gene can constitute or encode coding or non-coding sequences, sense or antisense sequences, including ribozymes, or catalytic RNA species such as described in the art (Hampel et al., *Nucleic Acids Research*, 18, 299–304 (1990); Cech et al., *Annual Rev. Biochem.*, 55, 599–629 (1986)), as well as engineered sequences, or sequences which are not normally present in vivo.

Similarly, the vectors employed in both the parallel and antiparallel recombination methods may include other genes or coding sequences. For instance, a coding sequence or a second coding sequence according to the invention can comprise the coding sequence of Cre or Flp, the coding sequence of EBNA-1, or any other coding sequence described herein.

In particular, the parallel and antiparallel recombination methods of the present invention can be employed to deliver Rep proteins to cells, either as a coding sequence, or a passenger gene. Various mutated Rep proteins and variations on the Rep coding sequence such as are known and have been reported in the literature (see, e.g., McCarty et al., *J. Virol.*, 66, 4050–7 (1992); Kyostio et al., supra) may be employed. In this fashion, the methods allow promotion of Rep-mediated recombination of sequences flanked by one or more adeno-associated virus ITRs (or sequences containing these ITRs that are known to those skilled in the art) into human chromosome 19 or into sequences that have been described in the art (see, e.g., Linden et al., *Proc. Natl. Acad. Sci.*, 93, 7966–7972 (1996)). The methods also can be employed to promote Rep-mediated recombination of sequences flanked by the adeno-associated virus ITRs into other genomic regions inasmuch as Rep proteins preferentially direct recombination into chromosome 19, but can direct recombination to other sites as well. Preferably the viral ITRs have been rendered deficient in packaging (e.g., Muzyczka, supra).

Any coding sequence (i.e., a first, second, or other coding sequence) or passenger gene according to the invention may be followed by sequences which allow production of a polycistronic message. There are a few ways in which such a polycistronic message—which reflects a highly efficient use of vector space—can be produced. For instance, a ribosome can essentially be recruited to the region of the AUG initiator codon of the second message by placing a 300–400 bp fragment from poliovirus in between the two coding regions. This allows cap-independent translation bypass, or translation of a non-capped message in a eukaryotic cell. Such a strategy (and hence, such similar sequences allowing use of the strategy in other species) has also been described in alpha mosaic plant virus. In a third approach to generation of a polycistronic message, a sequence of the cardiovirus is placed in frame between the coding sequences of the polycistronic message. No initiation codon (AUG) is required for the coding sequence of the downstream protein. Upon translation, the proteins are liberated by a mechanism under active investigation. Along the same lines, sequences allowing production of polycistronic messages also can be placed after the coding region of the coding sequence.

Thus, these approaches can be employed to generate a polycistronic message from the coding sequence, and coding sequences intervening between the first recombining site and the coding sequence. For instance, the EBNA-1 coding sequence (or some other coding sequence) can be the second open reading frame (ORF) in a dicistronic (or polycistronic) cassette that is activated by recombination. The viral promoter for EBV that drives expression of EBNA-1 provides only about 0.1% of the promoter activity observed with use of the CMV promoter. In a dicistronic cassette, however, the second gene is expressed at 0.1% of the first gene, and 10-fold above background. In this scenario, EBNA-1 would be induced by the recombination event. This is especially desirable in instances in which EBNA-1 expression during propagation of viral vectors may potentially act at oriP and destabilize the virus. Alternately, since oriP only replicates once per cell cycle, it can be possible in some circumstances to create a virus in which EBNA-1 is not regulated, but instead is under the control of a weak constitutive promoter.

Any suitable combination of recombining sites and recombinase can be utilized with the parallel and antiparallel recombination methods and vectors. Preferably, the first and second recombining sites comprise Lox sites, and the recombinase comprises Cre, or the first and second recombining sites comprise Frt sites, and the recombinase comprises Flp. Alternately, the recombinase can be another member of the $\lambda$ integrase family of recombinases (or any other appropriate recombinase), and the recombining site can be the corresponding sequence at which the recombinase acts. The recombinase can be provided to the cell by any suitable means, e.g., by locating the recombinase coding sequences on the delivery vector (for instance, as a coding sequence or passenger gene), coadministering a second vector which encodes the recombinase gene, or supplying exogenous recombinase.

Preferably the Cre coding sequence is comprised of the coding sequence of bacteriophage P1 recombinase Cre, or various mutations of this sequence such as described in the art (e.g., Wierzbicki et al., *J. Mol. Biol.*, 195, 785–794 (1987); Abremski et al., *J. Mol. Biol.*, 202, 59–66 (1988); Abremski et al., *J. Mol. Biol.*, 184, 211–20 (1988); Abremski et al., *Protein Engineering*, 5, 87–91 (1992) Hoess et al., *Proc. Natl. Acad. Sci.*, 84, 6840–6844 (1987); Sternberg et al., *J. Mol. Biol.*, 187, 197–212 (1986)), or the Cre protein supplied to cells is produced from one of these sequences by recombinant means. Further mutations of this coding sequence which are yet to be isolated also can be employed, so long as variant proteins resulting from such mutations are capable of effecting recombination at Lox sites. Furthermore, a nuclear localization signal can be appended to the Cre coding sequence to increase the concentration of Cre protein in the nucleus. Moreover, it is possible to co-supply to a cell vectors encoding complementary Cre or other mutant recombinase proteins, allowing for recombinase activity via intragenic or intergenic complementation. Assays for Cre function at Lox sites can be carried out as described by Abremski et al. (Abremski et al., *J. Biolog. Chem.*, 259, 1509–1514 (1984)) and Sauer et al. (Sauer et al. (1990), supra).

In terms of Cre/Lox driven recombination, preferably the loxP site is employed as a Lox site, or various mutations of this sequence are incorporated such as have been described in the literature (see, e.g., Mack et al., supra; Hoess et al. (1986), supra; Hoess et al., *Biochemistry*, 81, 1026–29 (1984); Hoess et al., *Gene*, 40, 325–329 (1985); Abremski et al., *J. Biolog. Chem.*, 261, 391–396 (1986)). Similar mutated sequences of loxP which are yet to be isolated also can be employed, so long as such sequences are capable of serving as recombining sites for Cre.

The first, or parallel, recombination method and the second, or antiparallel, recombination method may be better understood with reference to the accompanying drawings as referenced herein, particularly FIGS. 1A–1C through FIGS. 5A–5G which depict various illustrative embodiments of the parallel and antiparallel recombination vectors useful in the present inventive parallel and antiparallel recombination methods, respectively.

a. Parallel Recombination Method

Figure 1B:
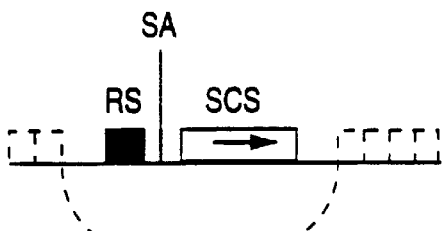
Figure 1C:
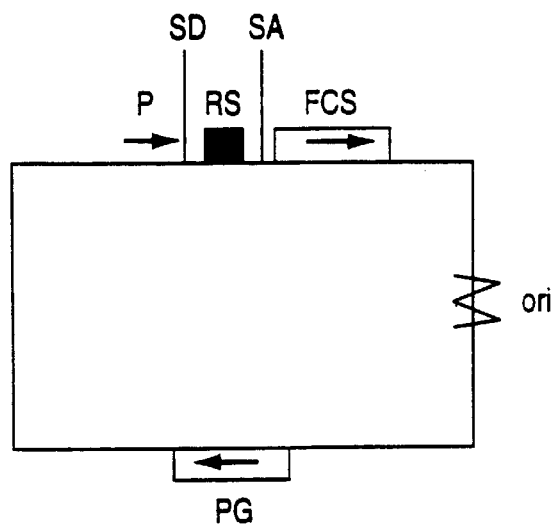
Figure 2A:
FIGS. 2A–2F are schematic diagrams depicting potential locations of the glycine-alanine (Gly Ala) repeats relative to the coding sequence (CS) and hormone binding domain (HBD). The glycine-alanine repeats similarly can be employed in the absence of any hormone binding domain.
Figure 2B:
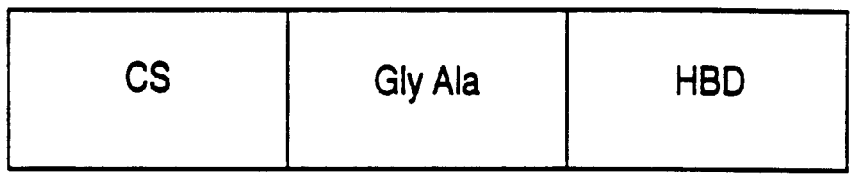
Figure 2C:
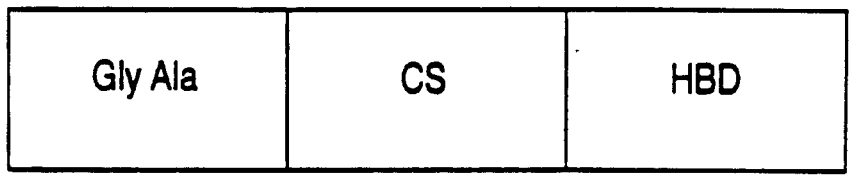
Figure 2D:
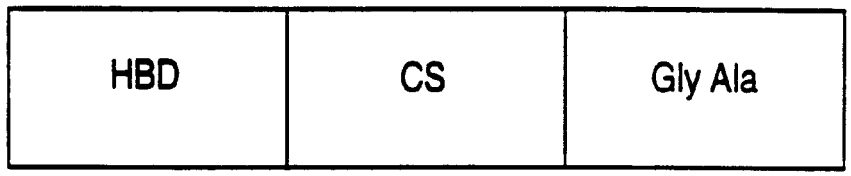
Figure 2E:
Figure 2F:
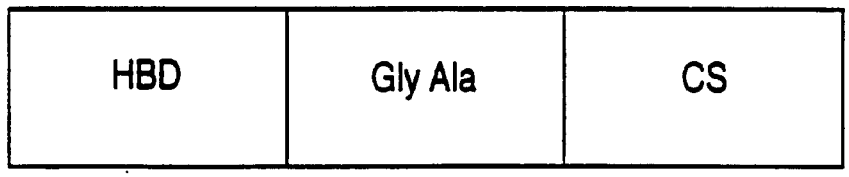

The parallel recombination method of the present invention allows for the generation of either a miniplasmid or an episome from an extrachromosomal genetic element. Whereas a miniplasmid does not replicate within a cell (and thus is of use where transient delivery or integration of a sequence is desired), an episome is capable of replicating extragenomically inside a cell. An episome is obtained when an origin or replication is present in the portion of the recombination substrate which is circularized as a result of the recombination event (as depicted in FIGS. 1A–1C); a miniplasmid is obtained when there is no such origin. The parallel recombination method thus has particular utility for viral vectors that are not stably maintained in cells as a consequence of their inability to integrate as proviruses into the host genome, or for viruses such as HSV whose genome is quiescent in the latent state. This method can be employed to obtain persistent gene expression by imparting stable maintenance in host cells upon passenger gene-carrying vectors which typically are not stably maintained, or are quiescent when latent, and also can be employed to modulate expression of genes carried by the vectors. Generally, there are three considerations for the delivery of episomes according to this method: (1) an origin of replication, (2) a means of excising the episome from the delivery vector, and (3) a method of ensuring segregation of a daughter molecule to each cell at mitosis.

Accordingly, the parallel recombination method of effecting site-specific recombination in a eukaryotic cell comprises: (a) contacting the cell with a vector comprising an origin of replication functional in mammalian cells located between first and second recombining sites located in parallel such that the vector is internalized by the cell, and (b) providing the cell with a site-specific recombinase that effects recombination between the first and second recombining sites of the vector.

As shown by way of the preferred vector depicted in FIG. 1A, either a linear virus (i.e., virus sequences indicated by the stippled boxes) or a circular molecule (i.e., plasmid or virus sequences indicated by the stippled line) can be utilized in conjunction with the parallel recombination method. In accordance with the aforementioned considerations for episome delivery, the parallel recombination method, and also, preferably, the antiparallel recombination method, can make use of an origin of replication functional in mammalian cells (e.g., an origin isolated from mammalian cells or a viral replication origin such as, but not limited to, a replication origin from Ad, HSV, EBV, papillomavirus, vaccinia virus, or polyomavirus. Accordingly, the present invention provides a set of vectors that will provide either a single integrated template, a low or intermediate number of episomes or miniplasmids per cell, or up to thousands of episomes per cell, each of which can comprise various coding sequences, promoters, and/or passenger genes, as described herein.

Desirably, vectors employed in the methods of the present invention possess an origin of replication which comprises a sequence of the EBV latent replicon, oriP, or variations on this sequence that are known and have been described in the art (e.g., Middleton et al., supra; Reisman et al., supra). This sequence can further comprise variations on the oriP sequence which are yet to be obtained, provided that such mutated sequences are capable of imparting autonomous replication on extragenomic DNA, as determined using methods known to those skilled in art (e.g., Middleton et al., supra; Reisman et al., supra). Moreover, in the parallel and antiparallel recombination methods, the origin of replication can be any replication origin capable of functioning in any cell, including non-eukaryotic or single-celled eukaryotic cells (e.g., prokaryotes and yeast) (see, e.g., M. Depamphilis, Ed., *DNA Replication in Eukaryotic Cells* (Cold Spring Harbor Press, NY, 1996)).

Notably, oriP serves a different biological function than do many origins of DNA replication that have been characterized from viruses. Namely, oriP permits controlled replication of plasmid DNA such that cell survival is not impaired. In contrast, other replication origins, termed "runaway replication origins", permit an exponential rate of DNA replication during the cell cycle, and ultimately can lead to cell death, depending on what other gene are present on the vector. Such runaway replication origins include but are not limited to the replicative origins of SV40, BK, polyomavirus, Ad, and HSV-1. These runaway replication origins also preferably can be employed in the methods and vectors of the present invention, and can be used for applications other than cell killing. Of course, other cofactors may need to be co-supplied to the cell for the origins to function properly in the cell.

In particular, with use of a polyomavirus runaway replication origin (e.g., as described by Muller, *Mol. Cell. Biol.*, 8, 5000–5015 (1988), and in GenBank Database Accession Number J02288 or PLY 2CG), viral large T antigen is required to initiate viral DNA replication. This protein acts by binding within the region of the replication origin, unwinding the DNA in this vicinity, and allowing other cellular enzymes (such as DNA polymerases) to act. Thus, with use of such a polyomavirus replication origin, at least viral T antigen preferably also is provided to the cell, for instance, as either a coding sequence (e.g., a first, second, or other coding sequence), or a passenger gene (i.e., in cis or in trans). Viral T antigen also can be provided exogenously. In some cases, it may be desirable to provide further permissive factors, e.g., to optimize viral replication. Desirably, the polyomavirus origin employed is a mouse polyomavirus origin. However, also preferably, the origin is a human, or other, polyomavirus origin. Sequences encoding these origins, as well as variations of these sequences, are known in the art (Muller, supra).

Similarly, an origin that permits a multicopy number of episomes per cell to be obtained can be employed. For instance, a papillomavirus origin (e.g., described in GenBank Database Accession Number PAPABPV1, with the BPV1 complete genome being described in GenBank Database Accession Number X02346, and the BPV4 early coding sequence being described in GenBank Database Accession Number D00146) can be used in the vectors of the invention. Papillomavirus genomes are maintained as multicopy plasmids in transformed cells. When such a papillomavirus origin is employed, desirably the viral E1 protein also is provided to the cell (e.g., as a coding sequence or passenger gene located in cis or in trans, or provided exogenously). In some cases, it also may be desirable to similarly supply the cell with a source of viral E2 protein to optimize replication. The papillomavirus origin and E1 and E2 proteins are known to those skilled in the art, and these sequences, or variations of these sequences, can be used (see, e.g., Pirsoo et al., *EMBO J.*, 15, 1–11 (1996), Grossel et al., *Virology*, 217, 301–310 (1996)). In particular, preferably the papillomavirus origin is that of a bovine. Alternately, preferably the papillomavirus is that of a human, but can be of any other source of the virus.

While these, and other, origins of replication that similarly impart ability on a circular DNA element to replicate autonomously within the host cell genome can be employed instead of oriP, when the oriP origin is employed, EBNA-1 also can be supplied to the cell. As for the other cell replication proteins, EBNA-1 protein can be provided exogenously, or the EBNA-1 coding sequence can be provided in cis or in trans to oriP, in the same manner as described for delivery of recombinase to the cell. Even though plasmids possessing oriP in the absence of EBNA-1 protein can be stably maintained in cells which have been infected with EBV (Lupton et al., supra; Teshigawara et al., *Nuc. Acids Res.*, 20, 2607 (1992)), the coding sequences for EBNA-1 together with oriP constitute the minimal requisite components for stable maintenance of a EBV-derived circular plasmid in cultured cells in the absence of EBV infection. Moreover, as described further herein, the parallel recombination method may be employed for delivery of Rep proteins (as well as other proteins) to a cell wherein an origin of replication is not utilized.

The excision of the episome or miniplasmid from the parallel recombination vector and its subsequent circularization is accomplished through application of a recombination system consisting of first and second recombining sites (FRS and SRS in FIG. 1A) within the vector, and a site-specific recombinase which acts at the first and second recombining sites to effect recombination between the first and second recombining sites of the vector. The presence of two recombining sites located in parallel on a single DNA molecule leads to excision by the appropriate recombinase of the intervening sequences so as to form a closed circular molecule. Partitioning of the episome between daughter cells can be accomplished through application of EBNA-1, which appears to act by binding to the host cell genome and oriP (or other origin of replication) and essentially pulling the episome into the nascent cell, or a protein having a similar function.

Accordingly, by encoding oriP, or another origin of replication functional in mammalian cells, between two parallel recombining sites in the vector, an episome will be generated by recombination upon appropriate application of the recombinase to the cell. Namely, upon providing the cell which has internalized the parallel recombination vector with such a site-specific recombinase, the parallel recombination vector (as exemplified by FIG. 1A) is recombined between the first and second recombining sites so as to form an episome (as exemplified in FIG. 1C). A miniplasmid similarly can be generated wherein there is no origin of replication present in between the parallel recombining sites. When a viral vector is employed as an episome or miniplasmid delivery vehicle, the second product of the recombination event (as exemplified in FIG. 1B) is a truncated virus, and when a plasmid is employed, a truncated plasmid, or miniplasmid, will similarly result.

Preferably, the vector further comprises the coding sequence for the recombinase, particularly the coding sequence for Cre. The vector also preferably can comprise one or more additional coding sequences, such as a first, second, and/or third coding sequence, and/or an additional coding sequence comprising a promoter, such as a passenger gene. Thus, in the parallel recombination method, the vector preferably further comprises a passenger gene. Optimally the passenger gene is located between the first and second recombining sites, as depicted in the parallel recombination vector of FIG. 1A, which results in an episome which carries the passenger gene (PG), as depicted in FIG. 1C.

Similarly, preferably the vector further comprises a coding sequence. Such a coding sequence can be any suitable coding sequence, optimally an EBNA-1 or Rep coding sequence, or various mutations of these sequences which are known and have been described in the art (see, e.g., Yates et al. (1985), supra; Lupton et al., supra, Middleton et al., *J. Virol.*, 66, 1795–1798 (1992); Levitskaya et al., supra). When replication origins other than oriP are employed, other viral replication proteins similarly can be provided as a coding sequence (e.g., large T antigen, E1, or E1 and E2). Desirably the coding sequence is located between the first and second recombining sites containing the replication origin, resulting in an episome carrying the coding sequence.

Along these lines, the parallel recombination method makes it possible to up- or down-regulate one coding sequence, or to simultaneously up-regulate one coding sequence and down-regulate another, through the recombination event. For instance, as depicted in FIG. 1A, a first coding sequence (FCS) can be located between the first and second recombining sites (FRS and SRS) and oriented to be transcribed in the direction from the first recombining site (FRS) to the second recombining site (SRS). On the same DNA molecule, a promoter (P) can be located between the FCS and SRS, such that P is capable of transcribing a coding sequence downstream of SRS. In such a situation, prior to recombination, the FCS will not be transcribed into nascent mRNA. However, following recombination, the FCS will be transcribed, as a consequence of the recombination event placing the FCS under the control of P.

The parallel recombination method also makes it possible to down-regulate transcription of one coding sequence simultaneous with up-regulation of another coding sequence, through the recombination event. Namely, if a second coding sequence (SCS) is located immediately downstream of P, and is operably linked to P such that P is capable of controlling the expression of the SCS, then prior to recombination, the SCS will be transcribed. After recombination, P, which previously commanded transcription of the SCS, will be placed upstream of the FCS, and the FCS will be transcribed, whereas the SCS will not be transcribed. It is not necessary, however, that the promoter control the expression of any downstream sequence prior to recombination. Similarly, it is not necessary that the promoter control expression of another coding sequence after recombination. This method can also allow independent down-regulation of a single coding sequence, e.g., by incorporating SCS in the vector of FIG. 1A in the absence of FCS.

Thus, in one embodiment of the parallel recombination method which can be employed to up-regulate a coding sequence, the method is preferably carried out wherein: (a) the coding sequence is located in the region between the first and second recombining sites which comprises the origin and adjoins the first recombining site such that the coding sequence is oriented to be transcribed in the direction from the first recombining site to the second recombining site proceeding through the coding sequence, (b) the coding sequence is not operably linked to any promoter, and (c) a promoter is located in the region between the first and second recombining sites which comprises the origin and adjoins said second recombining site such that the promoter is oriented to direct transcription in the direction from the first recombining site to the second recombining site proceeding through the promoter. Optimally there are no coding sequences, promoters, or transcription termination sites located between the first recombining site and the coding sequence.

Preferably, the vector employed to up-regulate expression of one coding sequence further comprises a second coding sequence located in a region other than the region between the first and second recombining sites which comprises said origin and adjoining the second recombining site, and which is operably linked to the promoter. This method allows for simultaneous up- and down-regulation of separate coding sequences. Optimally there are no coding sequences, promoters, or transcription termination sites located between the promoter and the second coding sequence.

In another embodiment of the parallel recombination method which can be employed to independently down-regulate a coding sequence in the absence of up-regulation of another sequence, the method is preferably carried out wherein: (a) a promoter is located in the region between the first and second recombining sites which comprises the origin and adjoins said second recombining site such that the promoter is oriented to direct transcription in the direction from the first recombining site to the second recombining site proceeding through the promoter, and (b) the coding sequence is located in a region other than the region between the first and second recombining sites which comprises the origin and adjoins the second recombining site such that the coding sequence is operably linked to the promoter.

These further methods also preferably can be employed when the episome delivery vector additionally carries a passenger gene. Moreover, to optimize production of protein encoded by the coding sequence following recombination, splice donor and acceptor sites can be included in the vector employed in the parallel recombination method.

According to this invention, any promoter (e.g., a promoter which is linked with a coding sequence as a consequence of recombination, as well as a promoter present as part of a passenger gene) whether isolated from nature, or produced by recombinant DNA or synthetic techniques, may be used to provide for gene transcription, so long as the promoter preferably is capable of directing transcription in a eukaryotic (desirably mammalian) cell.

The DNA sequences appropriate for expression in eukaryotic cells (i.e., "eukaryotic promoters") differ from those appropriate for expression in prokaryotic cells. Generally, eukaryotic promoters and accompanying genetic signals are not recognized in or do not function in prokaryotic systems and, prokaryotic promoters are not recognized in or do not function in eukaryotic cells.

A comparison of promoter sequences that function in eukaryotes has revealed conserved sequence elements. Generally, eukaryotic promoters transcribed by RNA polymerase II are typified by a "TATA box" centered around position −25 which appears to be essential for accurately positioning the start of transcription. The TATA box directs RNA polymerase to begin transcribing approximately 30 bp downstream in mammalian systems. The TATA box often functions in conjunction with at least two other upstream sequences located about 40 bp and 110 bp upstream of the start of transcription. Typically, a so-called "CCAAT box" serves as one of the two upstream sequences, and the other often is a GC-rich segment (e.g., a "GC box" comprised, for instance, of the sequence GGGCGG, or the sequences GCCACACCC and ATGCAAAT). The CCAAT homology can reside on different strands of the DNA. The upstream promoter element may also be a specialized signal such as those which have been described in the art and which seem to characterize a certain subset of genes.

To initiate transcription, the TATA box and the upstream sequences are each recognized by regulatory proteins which bind to these sites, and activate transcription by enabling RNA polymerase II to bind the DNA segment and properly initiate transcription. Base changes within the TATA box and the upstream sequences can substantially lower transcription rates (e.g., Myers et al., *Science*, 229, 242–7 (1985); McKnight et al., *Science*, 217, 316–324 (1982)). The position and orientation of these elements relative to one another, and to the start site, are important for the efficient transcription of some, but not all, coding sequences. For instance, some promoters function well in the absence of any TATA box. Similarly, the necessity of these and other sequences for promoters recognized by RNA polymerase I or III, or other RNA polymerases, can differ.

Accordingly, promoter regions vary in length and sequence, and can further encompass one or more DNA-binding sites for sequence-specific DNA binding proteins, and/or an enhancer or silencer. The present invention preferentially employs a CMV promoter, or a P5 promoter as a promoter for regulating a gene or coding sequence of interest (e.g., a "first coding sequence" or "second coding sequence" as described further herein). Such promoters, as well as mutations thereof, are known and have been described in the art (see, e.g., Hennighausen et al., *EMBO J.*, 5, 1367–1371 (1986); Lehner et al., *J. Clin. Microbiol.*, 29, 2494–2502 (1991); Lang et al., *Nucleic Acids Res.*, 20, 3287–95 (1992); Srivastava et al., *J. Virol.*, 45, 555–564 (1983); Green et al., *J. Virol.*, 36, 79–92 (1980); Kyöstiö et al., supra). Other promoters, however, can also be employed, such as the Ad2 or Ad5 major late promoter and tripartite leader, the Rous sarcoma virus (RSV) long terminal repeat, and other constitutive promoters such as have been described in the literature. For instance, the herpes thymidine kinase promoter (Wagner et al., *Proc. Natl. Acad. Sci.*, 78, 144–145 (1981)), the regulatory sequences of the metallothionine gene (Brinster et al., *Nature*, 296, 39–42 (1982)) promoter elements from yeast or other fungi such as the Gal 4 promoter, the alcohol dehydrogenase promoter, the phosphoglycerol kinase promoter, and the alkaline phosphatase promoter can be employed. Similarly, promoters isolated from the genome of mammalian cells or from viruses that grow in these cells (e.g., Ad, SV40, CMV, and the like) can be used.

Instead of using a constitutive promoter, the promoter also preferably can be up- and/or down-regulated in response to appropriate signals. For instance, an inducible promoter, such as the IL-8 promoter, which is responsive to TNF or another cytokine can be employed. Other examples of suitable inducible promoter systems include, but are not limited to, the metallothionine inducible promoter system, the bacterial lac expression system, and the T7 polymerase system. Further, promoters that are selectively activated at different developmental stages (e.g., globin genes are differentially transcribed in embryos and adults) can be employed. In particular, a promoter that can be regulated by exogenous factors such as tetracycline, or synthetic hormone such as RU-486 can be employed. These promoters (and accompanying regulatory factors that similarly can be provided to the cell) have all been described in the art (see, e.g., Delort et al., *Human Gene Therapy* 7, 809–820 (1996); Clontech, *CLONTECHniques*, "Tet-Off™ and Tet-On™ Gene Expression Systems and Cell Lines", Volume XI, No. 3, 2–5 (July 1996)).

Another option is to use a tissue-specific promoter (i.e., a promoter that is preferentially activated in a given tissue and results in expression of a gene product in the tissue where activated), such as the hepatocyte-specific promoter for albumin or $a_1$-antitrypsin (Frain et al., Mol. Cell. Biol. 10: 991–999 (1990); Ciliberto et al., Cell 41: 531–540 (1985); Pinkert et al., *Genes and Devel.*, 1, 268–276 (1987); Kelsey et al, *Genes and Devel.*, 1, 161–171 (1987)), the elastase I gene control region which is active in pancreatic acinar cells (e.g., Swift et al., *Cell*, 38, 639–646 (1984); MacDonald, *Hepatology*, 7, 425–515 (1987)), the insulin gene control region which is active in pancreatic beta cells (Hanahan, *Nature*, 315, 115–122 (1985)), the mouse mammary tumor virus control region which is active in testicular, breast, lymphoid and mast cells (Leder et al., *Cell*, 45, 485–495 (1986)), the myelin basic protein gene control region which is active in oligodendrocyte cells in the brain (Readhead et al., *Cell*, 48, 703–712 (1987)), and the gonadotropic releasing hormone gene control region which is active in the hypothalamus (Mason et al., *Science*, 234, 1372–1378 (1986)). Similarly, a tumor-specific promoter, such as the carcinoembryonic antigen for colon carcinoma (Schrewe et al., Mol. Cell Biol. 10: 2738–2748 (1990)) can be used in the vector. According to the invention, any promoter can be altered by mutagenesis, so long as it has the desired binding capability and promoter strength.

Additionally, it is now known that inducible activity can be obtained by fusing the C-terminal ligand binding domain of a hormone receptor onto the coding sequence of a particular protein (see, e.g., Kellendock et al., *Nucleic Acids Res.*, 24, 1404–1411 (1996); Metzger et al., *Proc. Natl. Acad. Sci.*, 92, 6991–6995 (1995)). This approach is advantageous in that when employed to create a recombinase fusion, it renders the recombination event inducible, and under the control of an exogenous substance that binds the steroid receptor. However, the method also preferably is employed with any coding sequence (e.g., a first and second coding sequence) according to the invention and/or any passenger gene. In particular, the method preferably is employed with use of a ligand binding domain (e.g., a hormone binding domain) of a hormone receptor that is capable of binding exogenous, but not naturally-occurring, steroid. For instance, the ligand binding domain of a mutant hormone progesterone receptor (hPR891) that responds to a low level of synthetic steroid such as RU-486, but not to endogenous steroid, can be employed (Kellendock et al., supra). Alternately, ligand binding domains from estrogen, glucocorticoid, and androgen receptors can be fused to the recombinase, or other coding sequence. Other similar approaches also have been described in the art and can be employed herein to render the activity of the recombinase or other protein encoded by a coding sequence according to the invention ligand-dependent, either through creation of translational fusions resulting in a chimeric protein, or through transcriptional fusions placing the gene under the control of an exogenous substance, as previously described. Moreover, unique proteins such as rapamycin allow the linkage of proteins that normally ignore each other, adding yet another level of control to the systems described herein (see, e.g., Balter et al., *Science,* 273, 183 (1996); Choi et al., *Science,* 273, 239–242 (1996)).

Furthermore, in some instance, the origins employed for autonomous replication of the vectors may also comprise sequences that function as promoters (e.g., due to the close intertwinement of DNA replication and transcription). For instance, the polyomavirus origin contains a constitutive promoter that can be employed, for instance to drive expression of a passenger gene. Similarly, the bovine papillomavirus origin of replication comprises a promoter that is induced by the papillomavirus E2 protein. This origin potentially can be used as a means of a gene within a vector according to the invention. Similarly, the EBV origin contains repeats that act as an enhancer in the presence of EBNA-1. These repeats can be employed, for instance, to up-regulate expression of a gene upon recombination-mediated up-regulation of EBNA-1.

The ordinary skilled artisan is aware that different genetic signals and processing events control levels of nucleic acids and proteins/peptides in a cell, such as, for instance, transcription, mRNA translation, and post-transcriptional processing. Transcription of DNA into RNA requires a functional promoter. The amount of transcription is regulated by the efficiency with which RNA polymerase can recognize, initiate, and terminate transcription at specific signals. These steps, as well as elongation of the nascent mRNA and other steps, are all subject to being affected by various other components also present in the cell, e.g., by other proteins which can be part of the transcription process, by concentrations of ribonucleotides present in the cell, and the like.

Protein expression is also dependent on the level of RNA transcription which is regulated by DNA signals, and the levels of DNA template. Similarly, translation of mRNA requires, at the very least, an initiation codon (preferably an AUG initiation codon) which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Molec. Biol.,* 196, 947–950 (1987)). Also, successful expression of a foreign nucleic acid sequence in a cell can require post-translational modification of a resultant protein/peptide. Thus, production of a recombinant protein or peptide can be affected by the efficiency with which DNA is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production following recombination, preferably the vector employed for simultaneous up- and down-regulation of separate coding sequences further comprises: (a) a splice acceptor site located between the first recombining site and the coding sequence in the region between the first and second recombining sites which comprises the origin, and (b) a splice donor site located between the promoter and the second recombining site in the region between the first and second recombining sites which comprises the origin, and (c) a splice acceptor site located between the second recombining site and the second coding sequence in a region other than that including the region between the first and second recombining sites which comprises the origin.

The ordinary skilled artisan also is aware that the immune response to certain immunogenic proteins can result in a decreased level of the protein in vivo. The Cre protein is an example of such a protein against which an immune response could be generated. In comparison, the EBV EBNA-1 protein efficiently escapes detection by the immune system. Accordingly, the present invention also provides a method of rendering Cre or other similar immunogenic proteins employed in the context of the invention invisible to the immune system. This method comprises placing copies of the glycine-alanine repeat of the EBNA-1 protein (or conservative variations thereof) at either the C- or N-terminus of the protein. Such placement preferably is done at the level of DNA in a coding sequence (e.g., of a first or second coding sequence, other coding sequence, or passenger gene). The glycine-alanine repeats are known in the art (see, e.g., Yates et al., supra; Lupton et al., supra; Levitskaya et al., supra). Preferably this is done by incorporating the nucleic acid sequence of the glycine-alanine repeats (or variants) at either the 5' or the 3' end of the coding sequence of interest. In particular, this approach also can be employed with use of a ligand binding domain, as previously described. As illustrated in FIGS. 2A–2F, the glycine-alanine repeats (Gly Ala) can be employed in a variety of locations vis-a-vis the coding sequence (CS) and ligand binding domain (HBD), if present.

The parallel recombination method can be employed to provide temporal regulation of genes and coding sequences. For instance, the first coding sequence can be an EBNA-1 or Rep coding sequence, as previously described. Also, the second coding sequence can comprise the coding sequence for Cre or Flp, as previously described. More generally, however, either the first or second (or other) coding sequence can comprise either the EBNA-1, Rep, Flp, Cre, large T antigen, E1, or E2 coding sequences.

The regulation effected due to the recombination event can be also employed to provide temporal expression of the recombinase coding sequence. Namely, the coding sequence for the recombinase can be located in the position of the SCS in FIG. 1A. Following excision of the episome, the recombinase will no longer be produced in the host cell. This approach is advantageous in that it is preferable that recombinase activity not occur following episome generation. This reduces the possibility of reintegration of the episome, or multimerization due to intermolecular recombination.

Along the same lines, the coding sequence for EBNA-1 can be located in the position of the FCS in FIG. 1A. This allows regulation of expression of the EBNA-1 coding sequence which is advantageous since EBNA-1-mediated replication of oriP in cis during viral production (i.e., when a virus is employed as the episome delivery vector) may, in some cases, lead to undesirable genome instability and a reduced yield. If the EBNA-1 coding sequence is provided as the FCS, then its expression will only occur after excision of the episome, when it is most needed.

Production of EBNA-1, or any protein encoded by a coding sequence whose transcription is commanded by P (i.e., FCS or SCS), can be maximized by placing SRS inside of an intron. This precludes the possibility of initiation at any fortuitous initiation codons present within SRS, and similarly precludes the formation of any fusion proteins. This can be accomplished, as illustrated in FIG. 1A, by locating splice acceptor sites (SAs) between FRS and FCS, and between SRS and SCS, and by also locating a splice donor site (SD) between P and SRS. Production of protein encoded by the FCS, SCS, or TG similarly can be maximized by positioning polyadenylation sites immediately downstream of the coding regions for these sequences.

The approach employed for controlling expression of EBNA-1 similarly can be employed as a means of controlling the transcription and subsequent translation of the Rep proteins from AAV. Temporal expression and expression levels of the Rep gene desirably is tightly regulated to avoid two potential problems. First, similar to EBNA-1, the presence of Rep proteins in the host cell during virus production could cause viral instability and decreased yields when a virus is employed as the episome delivery vector. Second, overexpression of the Rep gene is cytotoxic to the cell and could elicit an immune response. These potential problems can be avoided by cloning a Rep coding sequence into the position of the FCS in FIG. 1A. This will insure an absence of Rep gene expression during viral production. Upon infection and delivery of recombinase to cells containing the Rep-encoding vector (e.g., either by supplying the coding sequence for recombinase on the same vector, possibly as the SCS, or on a co-administered vector), recombination will occur, bringing P upstream of the Rep coding sequence, and placing the Rep coding sequence under the control of P. The P5 promoter, which is the natural promoter for the Rep gene, can be employed as P, since this promoter should command appropriate levels of Rep gene expression to allow Rep-mediated genomic integration without cytotoxic effects or eliciting an immune response.

Sequences flanked by one or more AAV ITRs are preferentially integrated into human chromosome 19 when Rep proteins are present. Thus in one embodiment of the method of the present invention, the coding sequence is a Rep coding sequence. Preferably the vector further comprises one or more (e.g., first and second) adeno-associated virus ITRs. In the method of the present invention, a variety of locations of the AAV ITRs can be employed inasmuch as, theoretically, the ITRs are location-independent. Accordingly, in this method, preferably one or more AAV ITRs are located in the region between the first and second recombining sites which comprises the origin. One or more ITRs, however, also can be located in a region other than the region between the first and second recombining sites which comprises the origin. The positioning of one or more AAV ITRs immediately flanking the passenger gene will allow integration of this gene into another genetic location. It is also possible to locate one or more AAV ITRs so that, upon Rep-directed recombination, Rep proteins are inactivated. For instance, one or more AAV ITRs can be placed between the FCS encoding Rep and a downstream polyadenylation site. In this case, Rep-mediated recombination of the episomal sequences into another genetic site would sever the Rep coding sequence from the polyadenylation site, thus abrogating Rep activity since transcripts are rapidly degraded in eukaryotic cells unless polyadenylated. Likewise, other genes similarly can be regulated, activated, or inactivated using the parallel recombination method of the present invention.

Alternately, Rep proteins can be delivered to the cell by providing them encoded on a miniplasmid generated using the parallel recombination method. This approach, as previously described, involves the generation of a miniplasmid on which Rep or another protein coding sequence is contained through the use of a vector comprising the sequence of interest located between two directly repeated recombining sites, wherein there is no origin of replication that similarly is located between the recombining sites.

Accordingly, the method of providing Rep proteins to a cell comprises: (a) contacting the cell with a vector comprising a Rep coding sequence located between first and second recombining sites located in parallel such that the vector is internalized by the cell, and (b) providing the cell with a site-specific recombinase that effects recombination between the first and second recombining sites of the vector. Optimally the Rep coding sequence is operably linked to a promoter within the vector, or is operably linked to a promoter within the vector as a consequence of the recombination event.

Preferably this method is carried out wherein: (a) the Rep coding sequence adjoins the first recombining site such that the coding sequence is oriented to be transcribed in the direction from the first recombining site to the second recombining site proceeding through the coding sequence, (b) the coding sequence is not operably linked to any promoter, and (c) a promoter is located in the region between the first and second recombining sites which comprises the coding sequence and adjoins the second recombining site such that the promoter is oriented to direct transcription in the direction from the first recombining site to the second recombining site proceeding through the coding sequence.

Also, preferably the vector employed for the delivery of Rep proteins further comprises first and second adeno-associated virus ITRs. Optimally one or more ITRs are located in the region between the first and second recombining sites which comprises the coding sequence. Alternately, one or more ITRs are located in a region other than the region between the first and second recombining sites which comprises the origin.

Figure 3A:
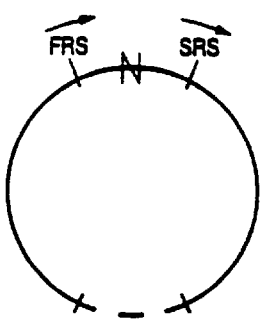
FIGS. 3A–3X are schematic diagrams depicting further applications according to the present invention of the parallel recombination method. The arrows indicate the direction of transcription. The stippling indicates that the vector can be either linear or circular. Open carrots indicate that the sequence specified can be present anywhere on the vector. Open bars within a defined region of the vector indicate the portion of the vector in which the sequence specified can be located. Abbreviations: RS, recombining site; FRS, first recombining site; SRS, second recombining site; SA, splice acceptor site; SD, splice donor site; FCS, first coding sequence; SCS, second coding sequence; TCS, third coding sequence; P, promoter; SP, second promoter; PG, passenger gene; N, origin of replication; ITR, inverted terminal repeat; Rep, Rep protein coding sequence.
Figure 3B:
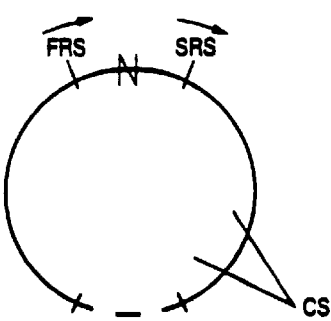
Figure 3C:
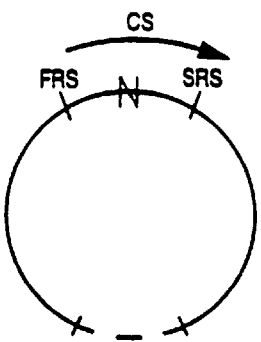
Figure 3D:
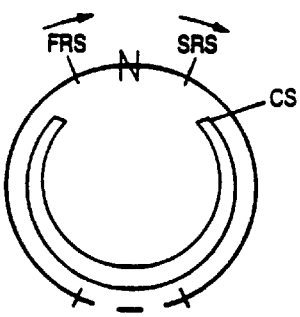
Figure 3E:
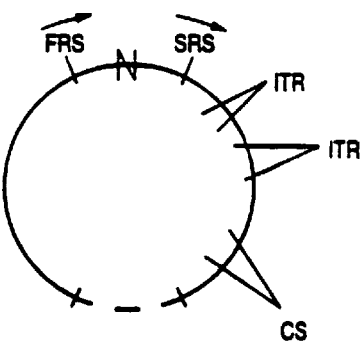
Figure 3F:
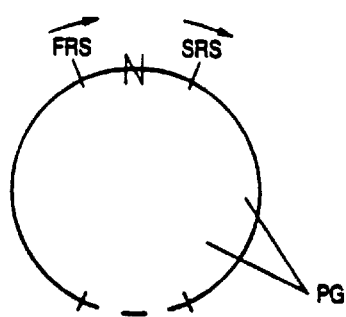
Figure 3G:
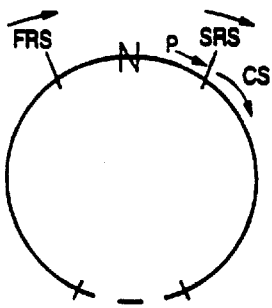
Figure 3H:
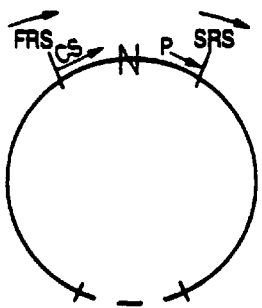
Figure 3I:
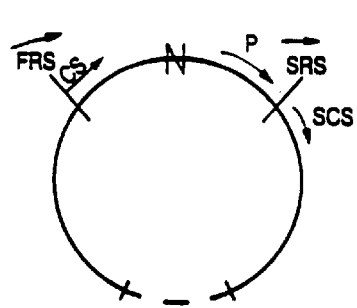
Figure 3J:
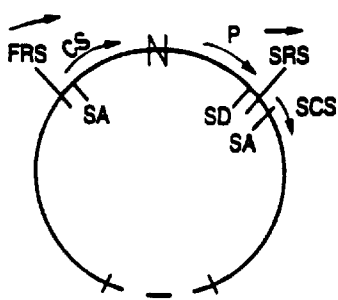
Figure 3K:
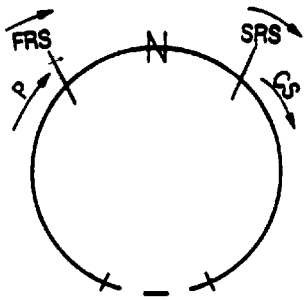
Figure 3L:
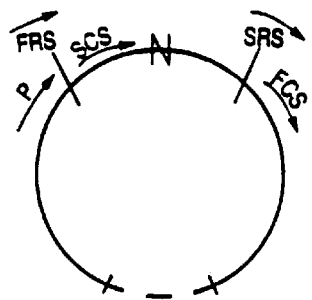
Figure 3M:
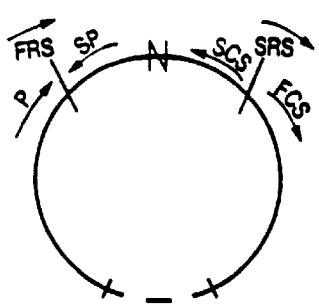
Figure 3N:
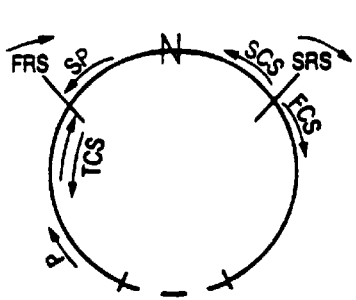
Figure 3O:
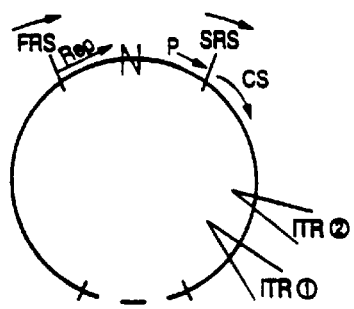
Figure 3P:
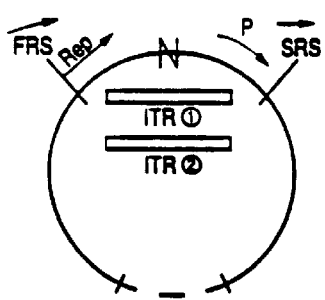
Figure 3Q:
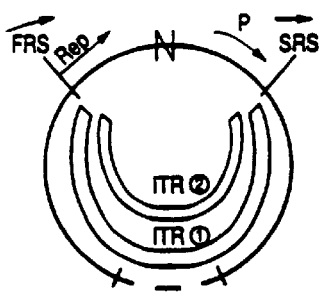
Figure 3R:
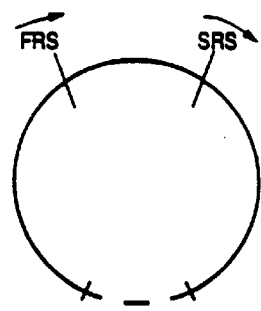
Figure 3S:
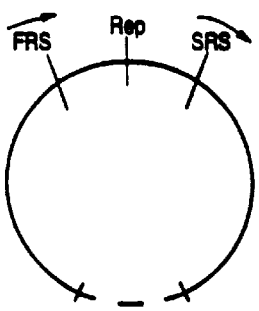
Figure 3T:
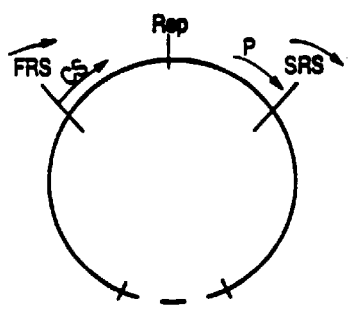
Figure 3U:
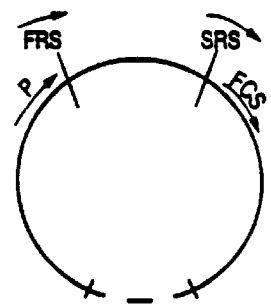
Figure 3V:
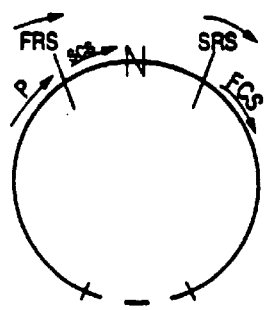
Figure 3W:
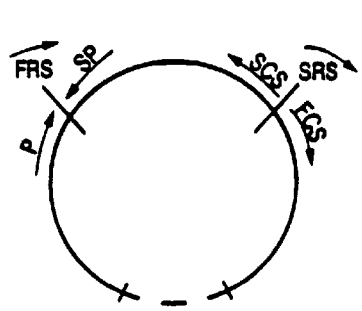
Figure 3X:
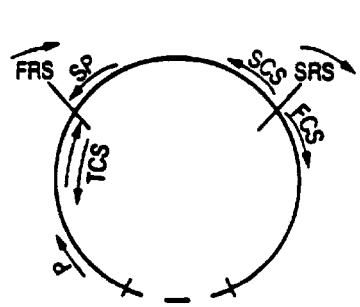

Some of these embodiments of the parallel recombination method are depicted in FIGS. 3A–3X. In particular, FIG. 3A depicts the method of the invention wherein a vector comprising parallel recombination sites (FRS and SRS), and an origin of replication located between these sites is provided to a cell. Recombinase also preferably is provided to the cell, either in cis or in trans. The vector (either linear or circular) employed in this method also preferably comprises a coding sequence (CS) that can be located anywhere on the vector (FIG. 3B), in the ori-containing region between the first and second recombining sites (FIG. 3C), or in a region other than the region between the first and second recombining sites (FIG. 3D). The vector further preferably can comprise one or more ITRs located anywhere on the vector (FIG. 3E), and/or can comprise one or more passenger genes (PG; FIG. 3F).

When a promoter is located in the region between the first and second recombining sites containing the origin, the parallel recombination method can be employed to down-regulate a coding sequence (FIG. 3G), up-regulate a coding sequence (FIG. 3H), or simultantaneously up-regulate a first coding sequence (CS) and down-regulate a second coding sequence (SCS; FIG. 3I) by the recombination event. One or more splice donor (SD) and/or splice acceptor (SA) sites can be incorporated into the vector to optimize protein production (FIG. 3J).

Regulation of gene expression effected by the recombination event similarly can be accomplished with use of a vector having a promoter located in a region other than the ori-containing region between the first and second recombining sites. Such a vector can be employed to up-regulate a coding sequence (FIG. 3K), or simultantaneously up-regulate a first coding sequence and down-regulate a second coding sequence (FIG. 3L) by the recombination event. The parallel recombination method also can be employed with use of a second promoter (SP) to simultaneously up-regulate a first and second coding sequence by the recombination event (FIG. 3M). Furthermore, a third coding sequence can be inserted in the vector, between the first promoter and first recombining site (FIG. 3N). In particular, when the third coding sequence is oriented in the same direction as the first promoter (FIG. 3N), a dicistronic message can be created by the recombination event (e.g., when an internal ribosome entry site also is appropriately located in the vector). When the third coding sequence is oriented in the opposite direction as the first promoter (FIG. 3N), the third coding sequence is down-regulated by the recombination event while the first coding sequence is up-regulated (e.g., optimally when splice donor and acceptor sites are appropriately located in the vector).

In particular, the parallel recombination method provides a convenient method for providing Rep protein to a cell, for instance, wherein the Rep gene is initially silent and is up-regulated by the recombination event (FIG. 3O). In this, as in other embodiments, the vector further can incorporate one or more ITRs located anywhere on the vector (FIG. 3O), in the ori-containing region between recombining sites (FIG. 3P), or outside of this ori-containing region (FIG. 3Q).

The parallel recombination method also can be carried out using a vector that does not comprise an origin of replication between the first and second recombining sites (FIG. 3R). Optionally, this method also can be carried out to deliver Rep to a cell, either as a passenger gene or coding sequence that is present on the minicircle formed by the recombination event (FIG. 3S). Such a vector further can comprise another coding sequence that is up-regulated by the recombination event (FIG. 3T). As with use of an ori-containing vector, the vector lacking the replication origin can be employed to up-regulate a coding sequence (FIG. 3U), simultaneously up-regulate a first coding sequence and down-regulate a second coding sequence (FIG. 3V), and up-regulate both a first and second coding sequence (FIG. 3W) by the recombination event. This embodiment also can be applied with use of a third coding sequence (FIG. 3X) as previously described. According to the invention, any of the coding sequences (i.e., first, second, or third) and/or the passenger gene can encode EBNA-1, Rep, Flp, Cre, large T antigen, E1, and E2 coding sequences. Further variations of this method will be apparent to one of skill in the art.

b. Antiparallel Recombination Method

The antiparallel recombination method is similar to that of the parallel recombination method in that it relies on site-specific recombination effected by a suitable recombination system, such as, preferably, the phage P1 Cre/Lox system, the yeast Flp/Frt system, or other appropriate recombination system. In contrast to the parallel recombination method, however, the antiparallel recombination method involves a vector with the first and second recombining sites located in an antiparallel orientation on the same DNA molecule. This alternate placement of the recombining sites leads to inversion of the intervening sequences upon application of the recombinase, instead of episome excision. The antiparallel recombination method can be employed to modulate gene expression, for instance, by providing for the up- or down-regulation of one coding sequence, or simultaneous up-regulation of one coding sequence and down-regulation of another coding sequence through the recombination event.

Along these lines, the antiparallel recombination method of effecting site-specific recombination in a cell comprises: (a) contacting the cell with a vector such that the vector is internalized by the cell, wherein the vector comprises (i) a promoter located between first and second recombining sites in antiparallel orientations and adjoining the second recombining site such that the promoter is oriented to direct transcription in the direction from the first recombining site to the second recombining site proceeding through the promoter, and (ii) a coding sequence located in a region other than the region between the first and second recombining sites which comprises the promoter and adjoining the first recombining site such that the coding sequence is oriented to be transcribed in the opposite direction from the direction of the first recombining site to the second recombining site proceeding through the promoter, wherein the coding sequence is not operably linked to any promoter; and (b) providing the cell with a site-specific recombinase that effects recombination between the first and second recombining sites of the vector. Preferably there are no coding sequences, promoters, or transcription termination sites located between the first recombining site and the coding sequence.

This method preferably further comprises a second coding sequence located in a region other than the region between the first and second recombining sites which comprises the promoter and adjoining the second recombining site, and which is operably linked to the promoter. Optimally there are no coding sequences, promoters, or transcription termination sites located between the promoter and the second coding sequence.

Moreover the antiparallel recombination method also can be employed to down-regulate a single coding sequence in the absence of up-regulation of another coding sequence. This method comprises: (a) contacting the cell with a vector such that the vector is internalized by the cell, wherein the vector comprises: (i) a promoter located between first and second recombining sites in antiparallel orientations and adjoining the second recombining site such that the promoter is oriented to direct transcription in the direction from the first recombining site to the second recombining site proceeding through the promoter, and (ii) a coding sequence located in a region other than the region between the first and second recombining sites which comprises the promoter and adjoining the second recombining site such that the coding sequence is operably linked to the promoter; and (b) providing the cell with a site-specific recombinase that effects recombination between the first and second recombining sites of the vector. Optimally there are no coding sequences, promoters, or transcription termination sites intervening between the promoter and the coding sequence following recombination.

Also, preferably, any of the vectors employed for up- and/or down-regulation of a coding sequence may further comprise a passenger gene, and/or the coding sequence of either the Rep, EBNA-1, Cre or Flp genes, as previously described. As for the parallel recombination method any coding sequence (e.g., first, second, or other coding sequence) and/or passenger gene can comprise the EBNA-1, Rep, Flp, Cre, large T antigen, E1, or E2 coding sequences.

Moreover, to optimize protein production following recombination, preferably the vector employed for simultaneous up- and down-regulation of separate coding sequences further comprises: (a) a splice acceptor site located between the first recombining site and the coding sequence in a region other than that including the region between the first and second recombining sites which comprises the promoter, (b) a splice donor site located between the promoter and the second recombining site in the region between the first and second recombining sites which comprises the promoter, and (c) a splice acceptor site located between the second recombining site and the second coding sequence in a region other than that including the region between the first and second recombining sites which comprises the promoter.

Figure 4:
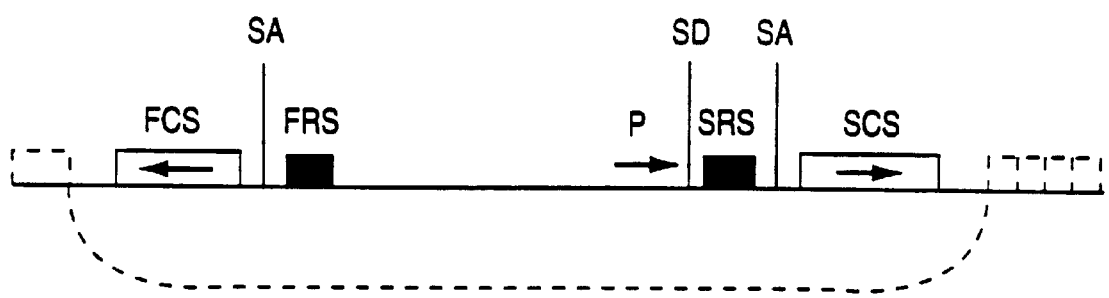
FIG. 4 is a schematic diagram depicting a vector with antiparallel recombining sites useful in the context of the present invention, particularly in the regulation of gene expression by site-directed recombination without episomal excision. Either a closed-circular vector (i.e., flanking plasmid or viral sequences indicated by the stippled line) or a linear vector (i.e., flanking viral sequences indicated by the stippled boxes) can be employed. The region between and including FCS to SCS can be in either orientation with respect to the flanking vector sequences. The arrows indicate the direction of transcription. Abbreviations: FRS, first recombining site; SRS, second recombining site; SA, splice acceptor site; SD, splice donor site; FCS, first coding sequence; SCS, second coding sequence; P, promoter.

FIG. 4 depicts a preferred vector for use in conjunction with the antiparallel recombination method. As illustrated in FIG. 4, the antiparallel recombination vector comprises a first coding sequence (FCS) adjoining the first recombining site (FRS) such that the FCS is oriented to be transcribed in the opposite direction from the first recombining site (FRS) to the second recombining site (SRS). The FCS is not transcribed, since it is not operably linked to any upstream promoter. A second coding sequence (SCS) is located adjoining the second recombining site (SRS), and is oriented to be transcribed in the direction from the first recombining site (FRS) to the second recombining site (SRS).

The SCS need not necessarily be present, for instance, in the case where the expression of one coding sequence is up-regulated, but another coding sequence is not down-regulated by the recombination event. However, when the SCS is present, it is transcribed, at least initially, since it is operably linked to a promoter (P) located between the first and second recombining sites (FRS and SRS). Similarly, the FCS need not necessarily be present, for instance, in the case where the expression of one coding sequence is down-regulated, but another coding sequence is not up-regulated by the recombination event. However, when the FCS is present, it is transcribed following recombination, which places P upstream of the FCS.

Thus, prior to the application of recombinase to a cell containing this vector, the SCS is transcribed, whereas the FCS is not transcribed. Following application of recombinase, the recombination event places P upstream of the FCS, and the FCS is transcribed whereas the SCS is not transcribed. Preferably there are no coding sequences, further promoters or transcription termination sites located between the FCS and the FRS, nor between the SCS and the SRS.

Moreover, to maximize gene expression and protein production, splice acceptor sites (SAs) can be placed between the FCS and the FRS, and between the SCS and the SRS. Moreover, a splice donor site (SD) can be placed between P and the SRS. Similarly, polyadenylation sites can be inserted following the coding regions of the FCS and SCS sequences.

In such a recombination method, preferably the SCS can encode a recombinase coding sequence, and preferably the FCS can encode a Rep coding sequence, or an EBNA-1 coding sequence. The antiparallel recombination vector illustrated in FIG. 4, and variations thereof, similarly can be employed for other genes, for instance for genes requiring proper temporal expression, such as developmentally-regulated genes, or for genes whose expression must be stringently controlled, such as those encoding toxic or deleterious proteins.

Moreover, in accordance with the antiparallel recombination method, it is also possible to up- and/or down-regulate a coding sequence (e.g., such as a coding sequence for Rep, EBNA-1 or recombinase) by placing the coding sequence in between the recombining sites, and placing one or more promoters outside the recombining sites. In one embodiment allowing for up-regulation, this method comprises: (a) contacting the cell with a vector such that the vector is internalized by the cell, wherein the vector comprises: (i) a coding sequence located between first and second recombining sites in antiparallel orientations and adjoining the second recombining site such that the coding sequence is oriented to be transcribed in the opposite direction from the direction of the first recombining site to the second recombining site proceeding through the coding sequence, and wherein the coding sequence is not operably linked to any promoter, and (ii) a promoter located in a region other than the region between the first and second recombining sites which comprises the coding sequence and adjoining the first recombining site such that the promoter is oriented to direct transcription in the direction from the first recombining site to the second recombining site proceeding through the coding sequence; and (b) providing the cell with a site-specific recombinase that effects recombination between the first and second recombining sites of the vector.

Preferably, to allow for simultaneous up- and down-regulation of separate coding sequences, the vector further comprises a second coding sequence located in the region between the first and second recombining sites which comprises the coding sequence and adjoining the first recombining site, and which is operably linked to the promoter.

Furthermore, in another embodiment providing for down-regulation of a single coding sequence, the method comprises: (a) contacting the cell with a vector such that the vector is internalized by the cell, wherein the vector comprises: (i) a coding sequence located between first and second recombining sites in antiparallel orientations and adjoining the first recombining site such that the coding sequence is oriented to be transcribed in the direction from the first recombining site to the second recombining site proceeding through the coding sequence, and (ii) a promoter adjoining the first recombining site and located in a region other than the region between the first and second recombining sites which comprises the coding sequence, such that the promoter is oriented to direct transcription in the direction from the first recombining site to the second recombining site proceeding through the coding sequence, and wherein the coding sequence is operably linked to the promoter; and (b) providing the cell with a site-specific recombinase that effects recombination between the first and second recombining sites of the vector.

Preferably these vectors may further comprise one or more passenger genes. Optimally there are no coding sequences, promoters, or transcription termination sites located between the promoter and the recombining site, or between the coding sequence or second coding sequence and the recombining site. Furthermore, splice sites (i.e., splice acceptor sites and splice donor sites) and polyadenylation sites can be incorporated in the vectors employed in these methods as previously described to maximize gene expression and production of encoded protein.

Figure 5A:
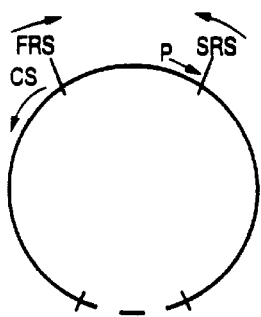
FIGS. 5A–5G are schematic diagrams depicting further applications according to the present invention of the antiparallel recombination method. The arrows indicate the direction of transcription. The stippling indicates that the vector can be either linear or circular. Abbreviations: RS, recombining site; FRS, first recombining site; SRS, second recombining site; SA, splice acceptor site; SD, splice donor site; FCS, first coding sequence; SCS, second coding sequence; P, promoter.
Figure 5B:
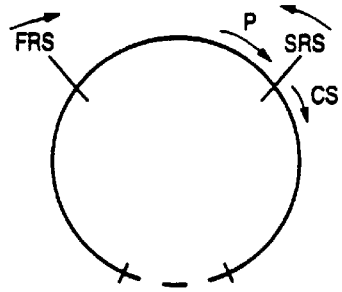
Figure 5C:
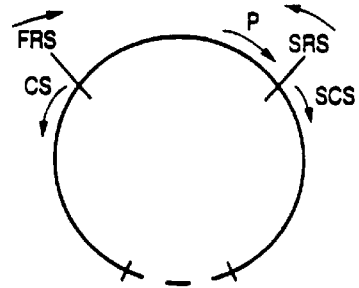
Figure 5D:
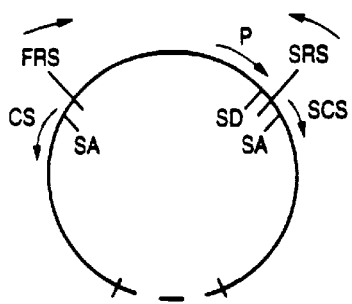
Figure 5E:
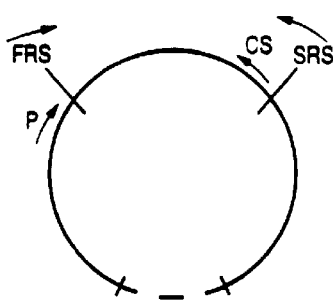
Figure 5F:
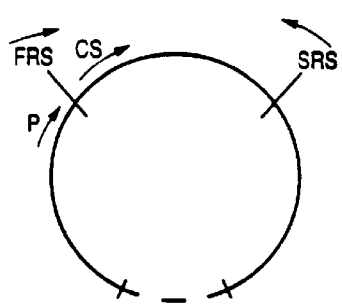
Figure 5G:
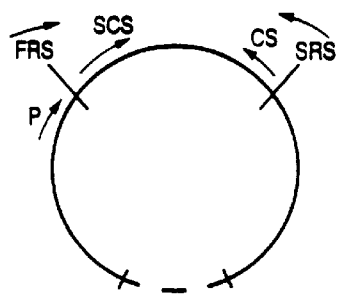

Some of these embodiments of the antiparallel recombination method are depicted in FIGS. 5A–5G. In particular, the method of the invention wherein a vector comprising antiparallel recombination sites (FRS and SRS) is provided to a cell is depicted. Recombinase also preferably is provided to the cell, either in cis or in trans. The vector (either linear or circular) employed in this method also preferably comprises a coding sequence (CS). When a promoter is located in the region between the first and second recombining sites, the antiparallel recombination method can be employed to up-regulate a coding sequence (FIG. 5A), down-regulate a coding sequence (FIG. 5B), or simultaneously up-regulate a first coding sequence (CS) and down-regulate a second coding sequence (SCS; FIG. 5C) by the recombination event. One or more splice donor (SD) and/or splice acceptor (SA) sites can be incorporated into the vector to optimize protein production (FIG. 5D).

Regulation of gene expression effected by the recombination event similarly can be accomplished with use of a vector having a promoter located in a region other than the ori-containing region between the first and second recombining sites (e.g., when a linear substrate is employed). Such a vector can be employed to up-regulate a coding-sequence (FIG. 5E), down-regulate a coding sequence (FIG. 5F), or simultaneously up-regulate a first coding sequence and down-regulate a second coding sequence (FIG. 5G) by the recombination event. According to the invention, any of the coding sequences (i.e., first, second, or any other coding sequence) and/or any passenger gene present in the vector can encode an EBNA-1, Rep, Flp, Cre, large T antigen, E1, or E2 coding sequence. Further variations of this method will be apparent to one of skill in the art.

Novel Vectors

While, as described above with respect to the present inventive methods, there are a variety of vectors which can be used in the context of the present invention, the present invention also provides certain novel vectors which are particularly useful in the present inventive parallel and antiparallel recombination methods.

The present inventive vector comprises first and second recombining sites, located in parallel or in antiparallel orientation. The first and second recombining sites can be any suitable recombining sites such that, after internalization by a cell and contact with a suitable recombinase, recombination will occur between the first and second recombining sites of the vector.

With respect to recombining sites, recombinase, coding sequences, regions between recombining sites, promoters, passenger genes, and the like, located on all vectors in the context of the present invention, such elements are as previously described and can be present as part of a cassette, either independently or coupled. In the context of the present invention, a "cassette" is simply a particular base sequence that possesses functions which facilitate subcloning and recovery of nucleic acid sequences (e.g., one or more restriction sites) or expression (e.g., polyadenylation or splice sites) of particular nucleic acid sequences.

Vector identification and/or selection can be accomplished using a variety of approaches known to those skilled in the art. For instance, vectors containing particular genes or coding sequences can be identified by hybridization, the presence or absence of so-called "marker" gene functions, and the expression of particular inserted sequences. In the first approach, the presence of a foreign sequence inserted in a vector can be detected by hybridization (e.g., by DNA-DNA hybridization) using probes comprising sequences that are homologous to the inserted nucleic acid sequence. In the second approach, the recombinant vector/host system can be identified and selected based upon the presence or absence of certain marker gene functions such as resistance to antibiotics, thymidine kinase activity, and the like, caused by the insertion of particular genes encoding these functions into the vector. In the third approach, vectors can be identified by assaying for the foreign gene product expressed by the inserted nucleic acid sequence. Such assays can be based on the physical, immunological, or functional properties of the gene product.

The present inventive vectors which are particularly useful in the parallel and antiparallel recombination methods are further described below.

a. Parallel Recombination Vector

In one embodiment, the present inventive parallel recombination vector comprises: (a) first and second recombining sites located in parallel, (b) an origin of replication located between the first and second recombining sites, (c) a coding sequence in the region between the first and second recombining sites which comprises the origin and adjoining the first recombining site such that the coding sequence is oriented to be transcribed in the direction from the first recombining site to the second recombining site proceeding through the coding sequence, the coding sequence is not operably linked to any promoter, and (d) a promoter located in the region between the first and second recombining sites which comprises the origin and adjoining the second recombining site such that the promoter is oriented to direct transcription in the direction from the first recombining site to the second recombining site proceeding through the promoter. Preferably there are no coding sequences, promoters, or transcription termination sites located between the first recombining site and the coding sequence.

Furthermore, preferably the vector further comprises a second coding sequence located in a region other than the region between the first and second recombining sites which comprises the origin and adjoining the second recombining site, and which is operably linked to the promoter. Optimally there are no coding sequences, promoters, or transcription termination sites located between the promoter and the second coding sequence. The vector further can comprise additional coding sequences, for instance a third coding sequence as previously described.

To optimize gene expression and protein production, the vector preferably further comprises: (a) a splice acceptor site located between the first recombining site and the coding sequence in the region between the first and second recombining sites which comprises the origin, and (b) a splice donor site located between the promoter and the second recombining site in the region between the first and second recombining sites which comprises the origin, and (c) a splice acceptor site located between the second recombining site and the second coding sequence in a region other than that including the region between the first and second recombining sites which comprises the origin. Such a vector provides a means of modulating gene expression by providing an episome in which the first coding sequence is up-regulated and the second coding sequence is down-regulated by the episome-forming recombination event.

In yet another embodiment, the present inventive parallel recombination vector comprises: (a) first and second recombining sites located in parallel, (b) an origin of replication located between the first and second recombining sites, (c) a promoter located in the region between the first and second recombining sites which comprises the origin and adjoins the second recombining site such that the promoter is oriented to direct transcription in the direction from the first recombining site to the second recombining site proceeding through the promoter, and (d) a coding sequence located in a region other than the region between the first and second recombining sites which comprises the origin and adjoining the second recombining site such that the coding sequence is operably linked to the promoter.

The recombining sites within the parallel recombination vector can be any suitable recombination sites as described above with respect to the present inventive methods. Preferably, the recombining sites within the parallel recombination vector are Lox sites, is in which event the parallel recombination vector preferably further comprises the coding sequence for Cre either upstream of the first Lox site or downstream of the second Lox site, or the recombining sites within the parallel recombination vector are Frt sites, in which event the parallel recombination vector preferably further comprises the coding sequence for Flp either upstream of the first Frt site or downstream of the second Frt site.

The origin of replication is as previously described and preferably comprises an EBV oriP sequence, a replication origin of polyomavirus or papillomavirus, or any other replication origin. With use of these (as well as other) replication origins, preferably further proteins that enable or facilitate cell replication can be provided to the cell. These further proteins, that in some sense can be considered "cell replication proteins", preferably are selected from the group consisting of the EBNA-1, large T antigen, E1, and E2 proteins.

The coding sequence can be any suitable coding sequence. Preferably, the first coding sequence is an EBNA-1 or Rep coding sequence, as described with respect to the present inventive methods. However, the first coding sequence (and the second coding sequence, or any other coding sequence) also preferably can comprise a Flp, Cre, large T antigen, E1, and/or E2 coding sequence. Such a vector provides a means of modulating gene expression by providing an episome in which the coding sequence is regulated by the episome-forming recombination event.

Preferably, the vector further comprises a passenger gene, which is preferably located between the coding sequence and the promoter. Any suitable passenger gene can be employed, such as a reporter gene or, most preferably, a therapeutic gene, as described in the context of the present inventive methods. Moreover, the invention provides further vectors as previously described and as illustrated in the accompanying Figures.

b. Antiparallel Recombination Vector

The present inventive antiparallel recombination vector is a vector comprising: (a) a promoter located between first and second recombining sites in antiparallel orientations and adjoining the second recombining site such that the promoter is oriented to direct transcription in the direction from the first recombining site to the second recombining site proceeding through the promoter, and (b) a coding sequence located in a region other than the region between the first and second recombining sites which comprises the promoter and adjoining the first recombining site such that the coding sequence is oriented to be transcribed in the opposite direction from the direction of the first recombining site to the second recombining site proceeding through the promoter, wherein the coding sequence is not operably linked to any promoter.

Preferably the vector further comprises a second coding sequence located in a region other than the region between the first and second recombining sites which comprises the promoter and adjoining the second recombining site, and which is operably linked to the promoter. Optimally there are no coding sequences, promoters, or transcription termination sites located between the first recombining site and the first coding sequence, or between the promoter and the second coding sequence.

Moreover, in another embodiment the present invention provides a vector comprising: (a) a promoter located between first and second recombining sites in antiparallel orientations and adjoining the second recombining site such that the promoter is oriented to direct transcription in the direction from the first recombining site to the second recombining site proceeding through the promoter, and (b) a coding sequence located in a region other than the region between the first and second recombining sites which comprises the promoter and adjoining the second recombining site such that the coding sequence is operably linked to the promoter.

To optimize gene expression and protein production, the antiparallel recombination vector further comprises: (a) a splice acceptor site located between the first recombining site and the coding sequence in a region other than that including the region between the first and second recombining sites which comprises the promoter, (b) a splice donor site located between the promoter and the second recombining site in the region between the first and second recombining sites which comprises the promoter, and (c) a splice acceptor site located between the second recombining site and the second coding sequence in a region other than that including the region between the first and second recombining sites which comprises the promoter.

Moreover, the present invention also provides an antiparallel recombination vector comprising: (a) a coding sequence located between first and second recombining sites in antiparallel orientations and adjoining the second recombining site such that the coding sequence is oriented to be transcribed in the opposite direction from the direction of the first recombining site to the second recombining site proceeding through the coding sequence, and wherein the coding sequence is not operably linked to any promoter, and (b) a promoter located in a region other than the region between the first and second recombining sites which comprises the coding sequence and adjoining the first recombining site such that the promoter is oriented to direct transcription in the direction from the first recombining site to the second recombining site proceeding through the coding sequence.

Preferably the vector further comprises a second coding sequence located in the region between the first and second recombining sites which comprises the coding sequence and adjoining the first recombining site, and which is operably linked to the promoter. The vector also preferably comprises other coding sequences (e.g., a third coding sequence, and/or other coding sequence), as previously described.

Furthermore, in another embodiment the vector comprises: (a) a coding sequence located between first and second recombining sites in antiparallel orientations and adjoining the first recombining site such that the coding sequence is oriented to be transcribed in the direction from the first recombining site to the second recombining site proceeding through the coding sequence, and (b) a promoter adjoining the first recombining site and located in a region other than the region between the first and second recombining sites which comprises the coding sequence, such that the promoter is oriented to direct transcription in the direction from the first recombining site to the second recombining site proceeding through the coding sequence, and wherein the coding sequence is operably linked to the promoter.

Preferably these vectors may further comprise a passenger gene. Optimally there are no coding sequences, promoters, or transcription termination sites located between the promoter and the recombining site, or between the coding sequence or second coding sequence and the recombining site. Furthermore, splice sites (i.e., splice acceptor sites and splice donor sites) and polyadenylation sites can be incorporated in the vectors employed in these methods as previously described to maximize gene expression and production of encoded protein.

Such a vector according to the invention provides a means of modulating gene expression without the generation of an episome as a consequence of the recombinase-driven recombination event. Further vectors as previously described and depicted in the accompanying Figures also are provided by the present invention.

Other General Considerations

In the methods of the present invention, in terms of provision of the various aspects of the invention to cells, vectors are transferred to a host cell, which is preferably a eukaryotic host cell. The eukaryotic host cell can be present in vitro or in vivo. According to the invention, "contacting" of cells with the vectors of the present invention can be by any means by which the vectors will be introduced into the cell. Preferably the viral vectors will be introduced by infection using the natural capability of the virus to enter cells (e.g., the capability of adenovirus to enter cells via receptor-mediated endocytosis). However, the viral and plasmid vectors can be introduced by any other suitable means, e.g., transfection, calcium phosphate-mediated transformation, microinjection, electroporation, osmotic shock, and the like. Similarly, in a preferred embodiment of the present invention, in vivo transfer of vectors is contemplated. Accordingly, the method of the present invention also contemplates vector transfer in vivo by the methods set forth herein, or by any standard method.

Also, according to the methods of the present invention, "providing the cell with a site-specific recombinase" encompasses providing the recombinase encoded by a vector, or providing the recombinase in the form of protein. Introduction of protein can be effected by any means appropriate for protein introduction to a cell, e.g., microinjection and adenoviral-mediated uptake for in vitro delivery, and injection or infusion or further means as described herein for in vivo delivery, as well as by other standard means of introduction known by those skilled in the art.

When practiced in vivo, any suitable organs or tissues or component cells can be targeted for vector or protein delivery. Preferably, the organs/tissues/cells employed are of the circulatory system (i.e., heart, blood vessels or blood), respiratory system (i.e., nose, pharynx, larynx, trachea, bronchi, bronchioles, lungs), gastrointestinal system (i.e., mouth, pharynx, esophagus, stomach, intestines, salivary glands, pancreas, liver, gallbladder), urinary system (i.e., kidneys, ureters, urinary bladder, urethra), nervous system (i.e., brain and spinal cord, and special sense organs such as the eye) and integumentary system (i.e., skin). Even more preferably the cells being targeted are selected from the group consisting of heart, blood vessel, lung, liver, gallbladder, urinary bladder, and eye cells.

For these embodiments, when one or more vectors are employed in the methods described herein, or when recombinase such as Cre or Frt is administered exogenously in the form of protein, the contacting of cells with the various components of the present invention can occur in any order or can occur simultaneously. Preferably the contacting will occur simultaneously. In a preferred embodiment, the component vectors of the present invention can be mixed together and preincubated prior to contacting the cell. When multiple vectors are to be administered, preferably the cell is contacted with the first vector less than about 6 weeks after, or less than about 6 weeks before, the cell is contacted with another vector. Even more preferably the cell is contacted with the first vector less than about 2 weeks after, or less than about 2 weeks before, the cell is contacted with another vector. When vectors are to be administered in combination with recombinase such as Cre or Frt, preferably the cell is contacted with the protein less than about 12 hours after, or less than about 12 hours before, the cell is contacted with a vector. Even more preferably the cell is contacted with the protein less than about 12 hours after, or less than about 12 hours before, the cell is contacted with a vector.

The composition of the present invention (i.e., a composition comprising the vectors and/or recombinases of the present invention) can be made into a pharmaceutical composition with appropriate pharmaceutically acceptable carriers or diluents, and where appropriate, can be formulated into preparations in solid, semi-solid, liquid or gaseous forms such as tablets, capsules, powders, granules, ointments, solutions, suppositories, injections, inhalants, and aerosols, in the usual ways for their respective route of administration. Means known in the art can be utilized to prevent release and absorption of the composition until it reaches the target organ, tissue, or cell, or to ensure timed-release of the composition. A pharmaceutically acceptable form should be employed which does not ineffectuate the composition of the present invention. In pharmaceutical dosage forms, the composition can be used alone or in appropriate association, as well as in combination with, other pharmaceutically active compounds.

Accordingly, the pharmaceutical composition of the present invention can be delivered via various routes and to various sites in an animal body to achieve a particular effect. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular effect to be achieved and the particular pharmacodynamics associated with the pharmaceutical composition in the particular host.

Accordingly, the present invention also provides a method of obtaining stable gene expression in a host, or modulating gene expression in a host, which comprises administering the composition of the present invention using any of the aforementioned routes of administration or alternative routes known to those skilled in the art and appropriate for a particular application. The "effective amount" of the composition is such as to produce the desired effect in a host which can be monitored using several end-points known to those skilled in the art. For example, one desired effect might comprise effective nucleic acid transfer to a host cell. Such transfer could be monitored in terms of a therapeutic effect (e.g. alleviation of some symptom associated with the disease or syndrome being treated), or by further evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). One such particularized assay described in the Examples which follow includes an assay for expression of the β-glucuronidase gene.

These methods described are by no means all-inclusive, and further methods to suit the specific application will be apparent to the ordinary skilled artisan. Moreover, the effective amount of the composition can be further approximated through appropriate assay of the recombination reaction, as previously described.

Generally, to ensure effective transfer of the vectors of the present invention, it is preferable that about 1 to about 5,000 copies of the vector be employed per cell to be contacted, based on an approximate number of cells to be contacted in view of the given route of administration, and even more preferable that about 1 to about 300 pfu enter each cell. However, this is merely a general guideline which by no means precludes use of a higher or lower amount of a component, as might be warranted in a particular application, Either in vitro or in vivo. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications depending on the particular cell type utilized or the means by which the vector is transferred. One skilled in the art easily can make any necessary adjustments in accordance with the necessities of the particular situation.

EXAMPLES

The following examples further illustrate the present invention but, of course, should not be construed as in any way limiting its scope.

Example 1

This example describes methods and vectors for site-specific recombination in a cell, and which can be employed to generate an episome, as set forth in FIGS. 1A–1C. In particular, this example demonstrates the method of episome delivery and up-regulation of gene transcription by the recombination event.

Standard molecular and genetic techniques such as generation of strains and plasmids, gel electrophoresis, DNA manipulations including plasmid isolation, DNA cloning and sequencing, Southern blot assays, and the like, were performed such as are known to those skilled in the art and as are described in detail in standard laboratory manuals (e.g., Maniatis et al., *Molecular Cloning: A Laboratory Manual,* 2nd ed. (Cold Spring Harbor, N.Y., 1992); Ausubel et al., *Current Protocols in Molecular Biology,* (1987)). Restriction enzymes and other enzymes used for molecular manipulations were purchased from commercial sources (e.g., Boehringer Mannheim, Inc., Indianapolis, Ind.; New England Biolabs, Beverly, Mass.; Bethesda Research Laboratories, Bethesda, Md.; etc.), and were used according to the recommendations of the manufacturer. Cells of the transformed human embryonic kidney cell line 293 (American Type Culture Collection CRL 1573) were cultured and maintained using standard sterile culture reagents, media and techniques, as previously described (Erzerum et al., *Nucleic Acids Research,* 21, 1607–1612 (1993)). Puromycin was employed, where appropriate, for election of transfected cells.

Figure 6:
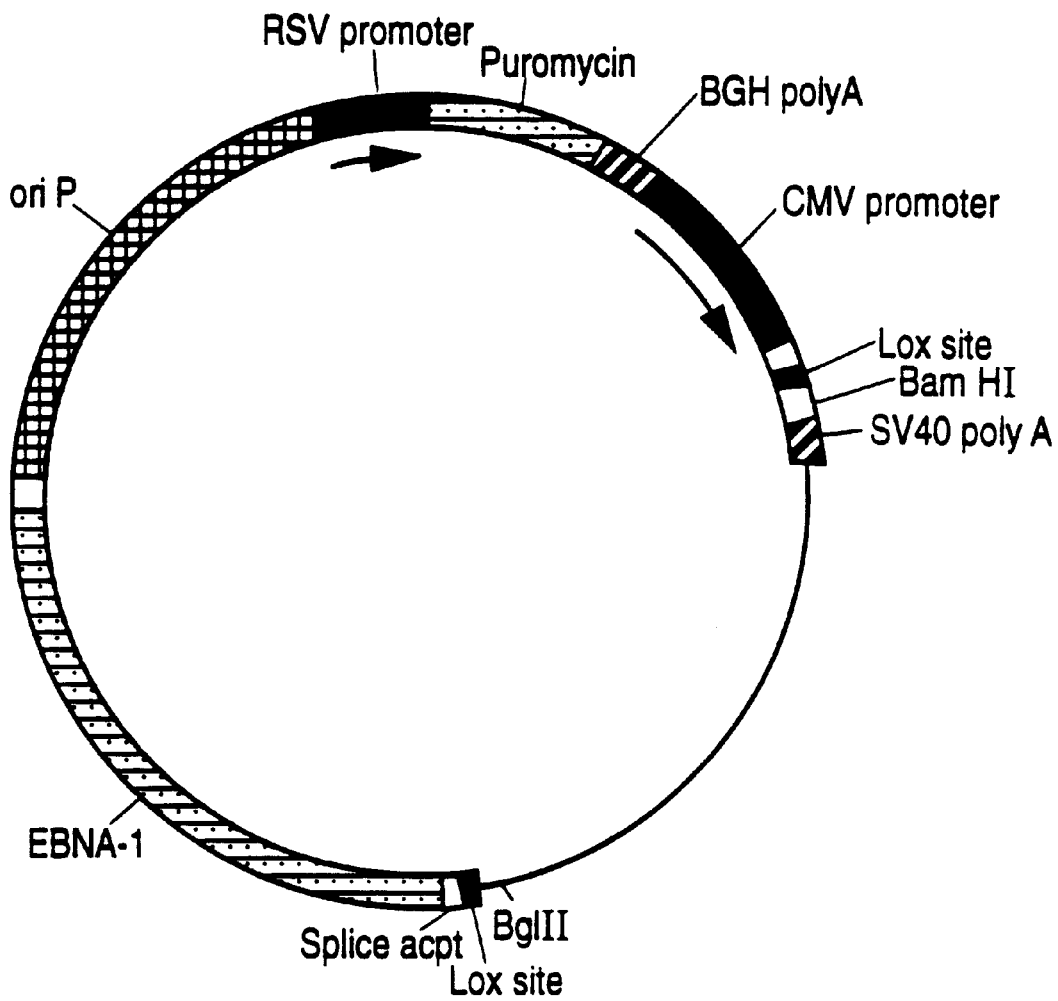
FIG. 6 is a restriction map depicting plasmid pEOBspLx-Puro-CMVLx.
Figure 7:
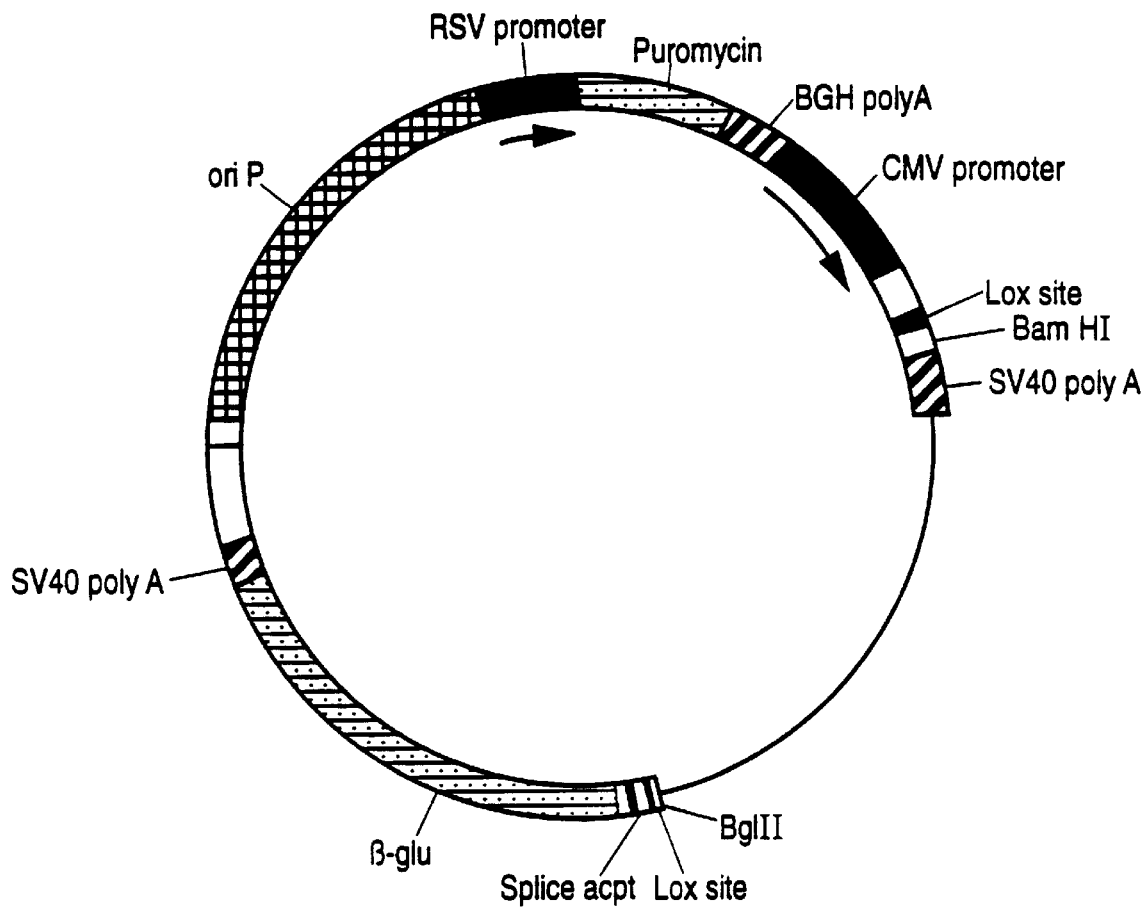
FIG. 7 is a restriction map depicting plasmid pEOBspLx-Puro-CMVLx-βglu.
Figure 8:
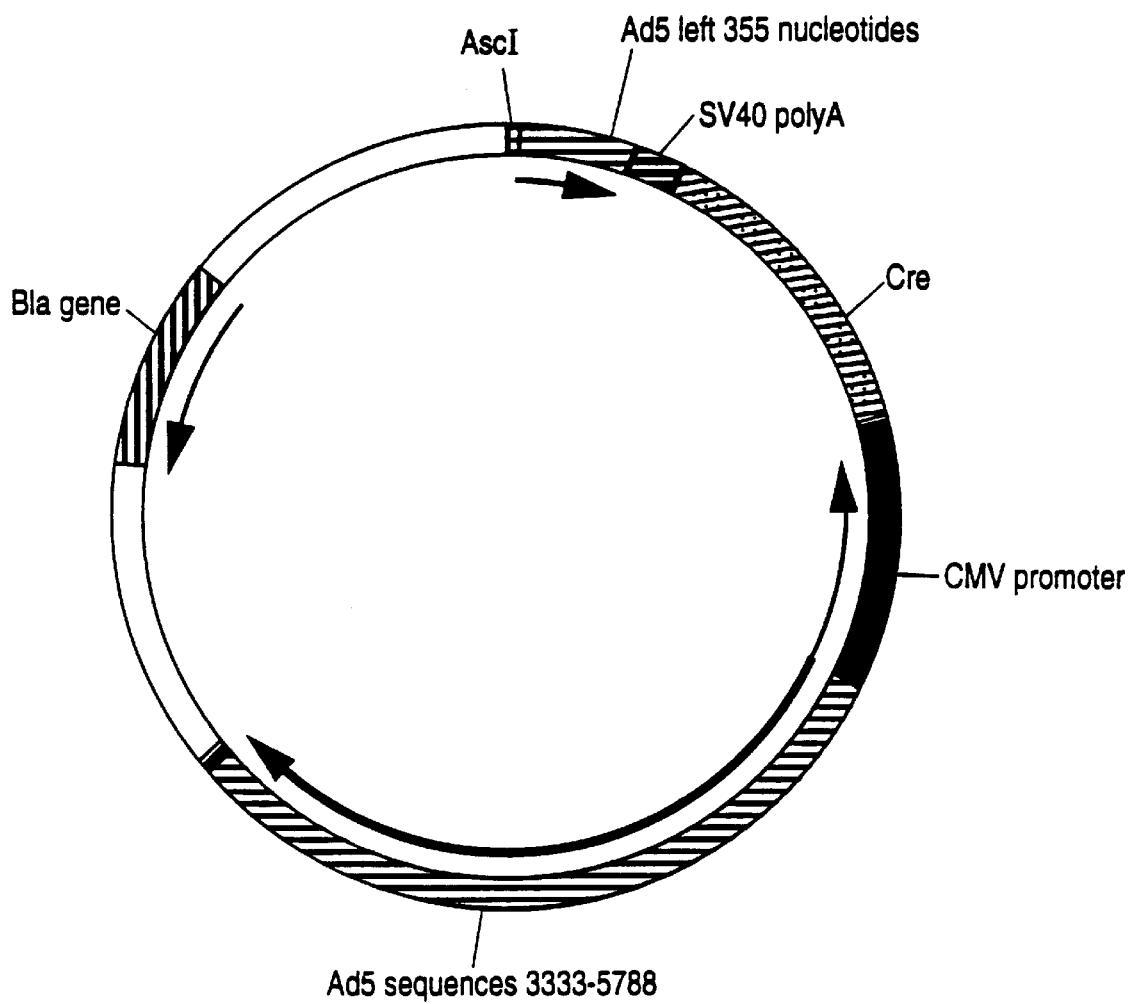
FIG. 8 is a restriction map depicting plasmid pAdCMV Cre.

Several plasmids were generated to test and confirm the method of the present invention as set out in FIGS. 1A–1C. These plasmids include pEOBspLx-Puro-CMVLx, which comprises as the FCS the EBNA-1 coding sequence, and which is depicted in FIG. 6. Plasmid pEOBspLx-Puro-CMVLx-βglu is depicted in FIG. 7, and comprises as the FCS the β-glucuronidase coding sequence. Both plasmids pEOBspLx-Puro-CMVLx and pEOBspLx-Puro-CMVLx-βglu comprise Lox sites (in parallel) as the recombining sites, and include a CMV promoter as a promoter for up-regulating gene expression. The CMV promoter was employed since it is able to drive a relatively high level of constitutive gene expression in most tissue culture cells (Boshart et al., Cell, 41, 521–530 (1985)). Similarly, both plasmids pEOBspLx-Puro-CMVLx and pEOBspLx-Puro-CMVLx-βglu comprise the puromycin coding sequence under the control of the RSV promoter. The Cre-expressing plasmid pAdCMV Cre, which places the phage P1 Cre coding sequence under the control of the CMV promoter and SV40 polyadenylation signal is depicted in FIG. 8.

Plasmid pEOBspLx-Puro-CMVLx was generated from Invitrogen's pREP 4 vector (Invitrogen, San Diego, Calif.). pREP 4 was restricted with HpaI and BsmI, and an oligonucleotide containing the restriction sites MluI, PvuII and KpnI was introduced after the unique MluI site in the vector was modified. A cassette containing a puromycin gene under the control of the RSV promoter and bovine growth hormone (BGH) polyadenylation signal was cloned on a MluI/PvuII DNA fragment into the vector backbone. A CMV promoter containing a splice signal followed by a polylinker and a SV40 polyadenylation sequence was introduced into the PvuII/KpnI sites of the vector backbone. A Lox site was introduced into the intron of the CMV expression cassette. Sequences upstream of the EBNA-1 coding sequence were modified by the addition of a synthetic splice acceptor site and Lox site. The splice acceptor site is proximal to EBNA-1 in pEOBspLx-Puro-CMVLx.

Plasmid pEOBspLx-Puro-CMVLx-βglu is derived from pEOBspLx-Puro-CMVLx by replacing the coding sequence for EBNA-1 with the β-glucuronidase coding sequence and SV40 polyadenylation signal. The resultant deletion in the EBNA-1 coding sequence spans the region from the initiation codon to the EBNA-1 BsgI site.

Plasmid pAdCMV Cre contains an expression cassette comprising the CMV promoter, Cre coding sequence and SV40 polyadenylation site flanked by Ads sequences 1–355 and 3333–5788. Of course, the precise limits of the sequences employed for recombination can vary (e.g., from about 1 to about 100 bp) depending on the particular recombination product desired. The pAdCMV Cre plasmid can be recombined with Ad to generate an E1-deficient virus (see, e.g., Rosenfeld et al. (1991), supra; Rosenfeld et al. (1992), supra).

To test the ability to select for cells containing pEOBspLx-Puro-CMVLx-βglu by selecting for puromycin resistance imparted by the RSV/puromycin cassette, CaPO$_4$-mediated transfections into EBNA-1 expressing-293 cells (293-EBNA; InVitrogen, San Diego, Calif.) of pEOBspLx-Puro-CMVLx-βglu were carried out. Following transfection, cells were maintained in the presence of puromycin at a concentration of about 0.5 mg/ml. The surviving cell population was puromycin resistant due to puromycin expression from the RSV/puromycin cassette.

CaPO$_4$-mediated transfections into 293 cells of pEOBspLx-Puro-CMVLx-βglu with or without pAdCMV Cre were carried out (Graham et al., J. Gen. Virol., 36, 59–72 (1977)) to determine whether Cre recombinase produced by the Cre gene supplied in trans to 293 cells could effect recombination between Lox sites present in pEOBspLx-Puro-CMVLx-βglu, thus generating an episome and placing the β-glucuronidase coding sequence in the episome under the control of the CMV promoter. After 48 hours, the cells were processed and assayed for β-glucuronidase activity using a commercial kit according to the recommendations of the manufacturer (Tropix Inc., Bedford, Mass.). The obtained results are set forth in Table 2.

TABLE 2

Levels of β-glucuronidase following transfection.

| Plasmid(s) | β-glucuronidase units |
| --- | --- |
| No Plasmid | 850 |
| pECBspLx-Puro-CMvLx-βglu | $6.9 \times 10^3$ |
| pEOBspLx-Puro-CMvLx-βglu + pAdCMV Cre | $1.6 \times 10^5$ |

As set forth in Table 2, β-glucuronidase levels are highest in those cells containing both pEOBspLx-Puro-CMVLx-βglu and pAdCMV Cre. In the absence of both pEoBspLx-Puro-CMVLx-βglu and pAdCMV Cre (i.e., the "no plasmid" condition), β-glucuronidase levels are barely detectable in 293 cells, although a low basal level of activity is observed. In comparison, a higher level of β-glucuronidase is observed in pEOBspLx-Puro-CMVLx-βglu-containing cells in the absence of pAdCMV Cre.

Subsequently, it was discovered that the recombining sites in pEOBspLx-Puro-CMVLx-βglu are in an antiparallel orientation instead of the parallel orientation. Thus, the β-glucuronidase activity observed ostensibly was due to the presence of a cryptic promoter placed upstream of the reporter gene by the recombination event. However, these results do confirm that the method of the invention can be employed to obtain an antiparallel recombination vector.

Example 2

This example describes vectors for site-specific recombination in a cell, and which can be employed to generate an episome, as set forth in FIGS. 1A–1C. More particularly, this example describes such vectors which are linear Ad vectors.

The method of the present invention similarly can be employed for viral episome delivery vectors, particularly Ad episome delivery vectors, through modification of the vectors and approach described in the prior example. Namely, the functionality of oriP, or a similar origin of replication capable of functioning in mammalian cells, in such a viral vector can be confirmed by transfecting pEOBspLx-Puro-CMVLx-βglu into a cell line that constitutively expresses EBNA-1 (such as described in Reisman et al., supra). Cells resistant to puromycin can be selected and expanded. Southern blot analysis can be employed to confirm the maintenance of the plasmid as an episome. The functionality of EBNA-1 can be similarly confirmed.

To generate the Ad vectors, both the EBNA-1 and β-glucuronidase-based plasmids can be transferred into a shuttle vector and constructed in a similar fashion as pAdCMV Cre. Basically, the shuttle vector comprises a stuffer fragment flanked by BclI and BamHI restriction sites surrounded on one side by the left 355 bp, and on the other side by residues 3333–5788 from Ads. The stuffer fragment was replaced with the BglII to BamHI restriction fragment harboring both Lox sites from pEOBspLx-Puro-CMVLx generating plasmid pAdER-Puro. Similarly, the stuffer fragment can be replaced with the BglII to BamHI restriction fragment harboring both Lox sites from pEOBspLx-Puro-CMVLx-βglu. Either of these plasmids can then be used to generate Ad5-based vectors by homologous recombination as previously described (see, e.g., Rosenfeld et al. (1991), supra; Rosenfeld et al. (1992), supra).

Example 3

This example describes further vectors that can be employed for effecting site-specific recombination in a cell. In particular, this example describes a representative example of a vector that can be employed to provide Cre recombinase.

Figure 9:
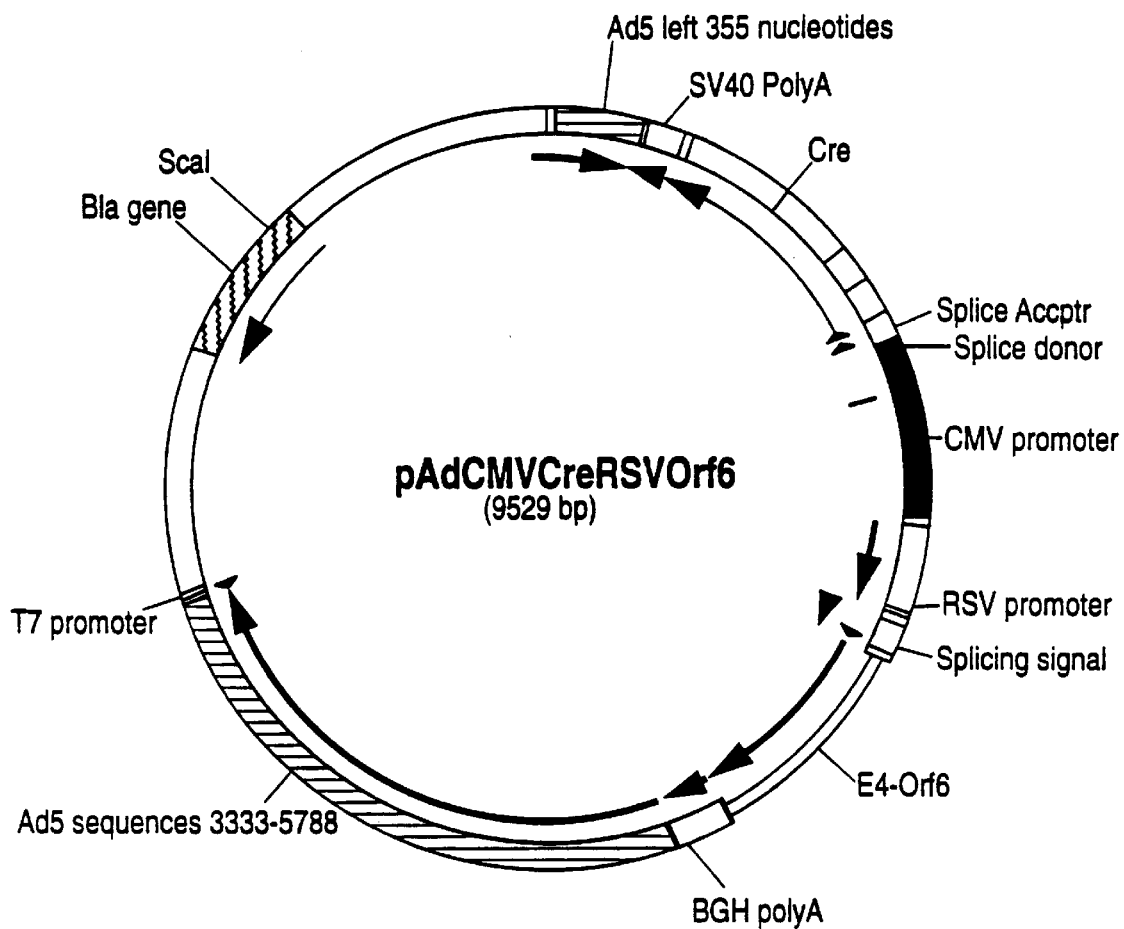
FIG. 9 is a restriction map depicting plasmid pAdCM-VCreRSVOrf6.

To facilitate vector construction, and particularly the vector depicted in FIGS. 1A–1C, the Cre gene was subcloned into a separate Ad. P1 obtained from ATCC was used as the source of the Cre recombinase coding sequence, which was cloned into pCR-Script™ (Stratagene, La Jolla, Calif.) using PCR to provide a more accessible source of the gene. The Cre gene was then transferred into a shuttle vector in which it was placed under the control of the CMV promoter, and followed by a SV40 polyadenylation signal to generate vector pAdCMVCreRSVOrf6 depicted in FIG. 9. The shuttle vector was used to generate the Ad vector AdCMVCre6 (using the methods previously described), in which the Cre gene replaces the E1 region of the adenoviral genome.

Production of AdCMVCre6 was confirmed by PCR and with use of a functional assay as described in Example 1. Namely, Southern blot analysis of AdCMVCre6-directed recombination was validated with use of a test plasmid in both the 293-based cell line 835, as well as in the human lung carcinoma cell line A549. Similarly, the functioning of the promoter, splice donor, and splice acceptor sites used in the various constructs of this and the previous Examples also were confirmed. In particular, β-glucuronidase was placed in position of the first coding sequence in FIG. 1A to generate the plasmid pEOBglug1. Cotransfection of pEOBglug1 with a Cre-expressing plasmid resulted in more than a 3-log induction of β-glucuronidase.

These results confirm the functionality of Cre recombinase in this vector, and further confirm the functionality of the base vector components used for subsequent vector constructions.

Example 4

This example describes further vectors for use for effecting site-specific recombination in a cell. In particular, this example describes vectors that comprise a polyomavirus origin of replication and that can be used, for instance, to obtain runaway replication.

The vectors containing the polyomavirus origin were constructed using standard cloning techniques as described in the previous Examples. The functioning of the components of the EBV and polyomavirus systems contained in the various vectors and required for replication (in particular, the origin of replication) was confirmed with use of a Dpn I assay. The basis of this assay is that plasmids produced in *E. coli* are methylated and are sensitive to restriction by Dpn I. In comparison, if the plasmid replicates in mammalian cells, it either is hemimethylated, or is not methylated at all, which renders it resistant to Dpn I restriction.

Figure 10:
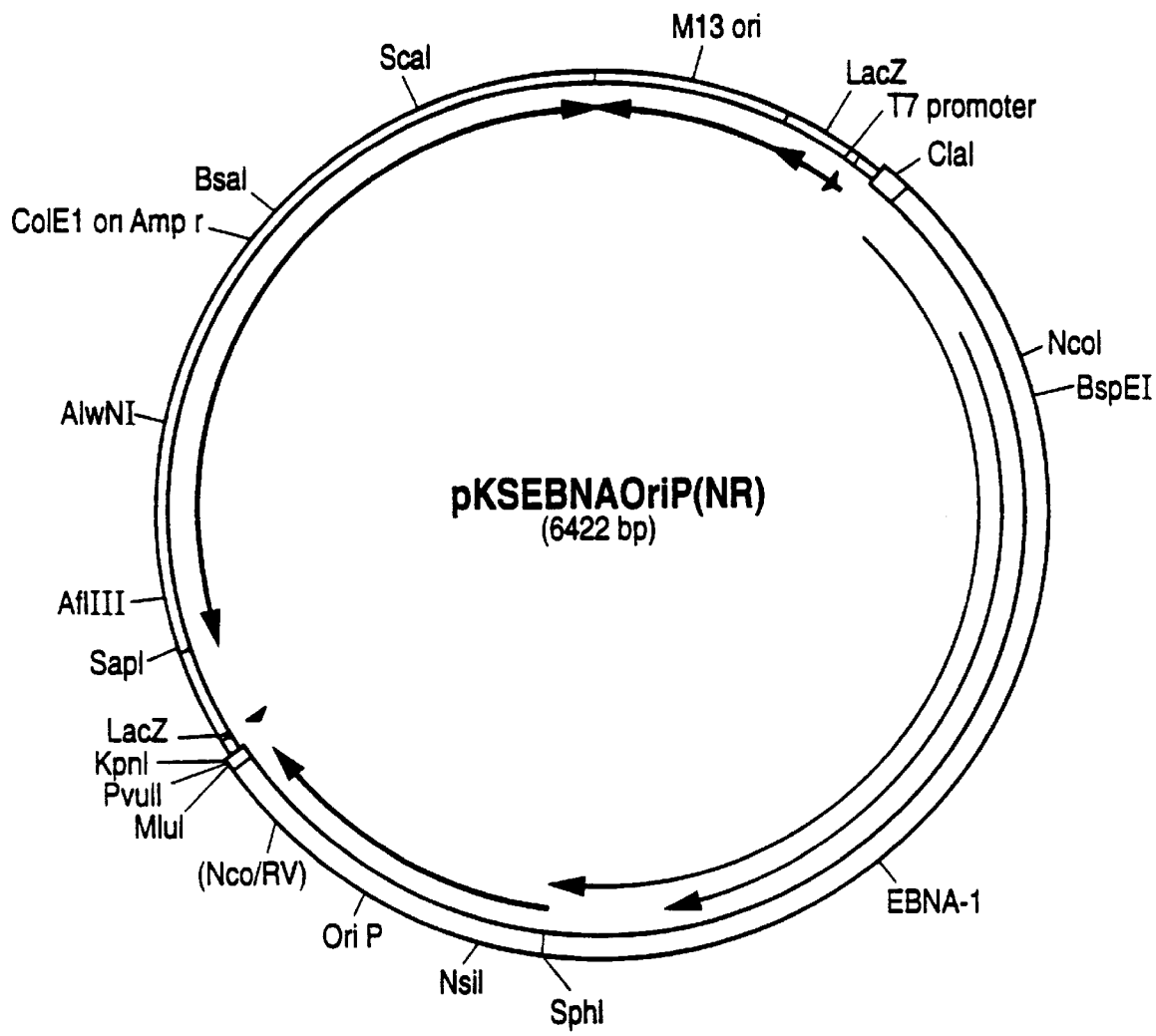
FIG. 10 is a restriction map depicting plasmid pKSEBNAOriP(NR).
Figure 11:
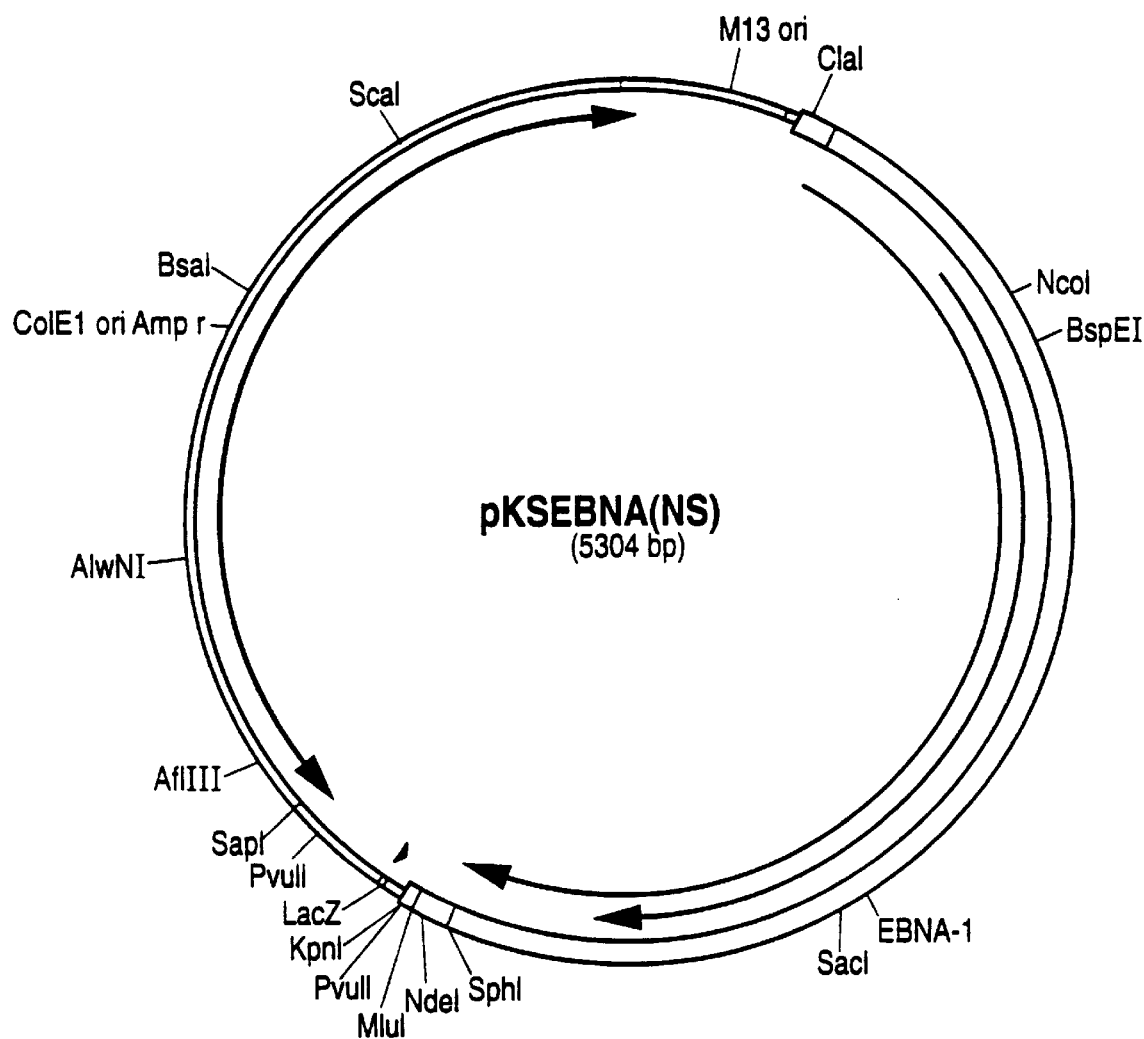
FIG. 11 is a restriction map depicting plasmid pKSEBNA (NS).

The isogenic constructs pKSEBNAOriP(NR) (depicted in FIG. 10) and pKSEBNA(NS) (depicted in FIG. 11) were tested to confirm functionality of the EBV component. These plasmids contain EBNA-1 under the control of its own viral promoter in either the presence (i.e., plasmid pKSEBNAOriP(NR)) or absence (i.e., plasmid pKSEBNA (NS)) of oriP located immediately 5' of the gene. The oriP origin in pKSEBNAOri(NR) has a deletion from Nco I to Eco RV (i.e., EBV coordinates 8033 to 8995), resulting in a 962 bp deletion. The plasmids were transfected into 293-derived cells and harvested 5 days later. The cell pellets were subjected to Hirt extraction (Hirt, *J. Mol. Biol.*, 26, 365–369 (1967)), and the Dpn I assay was performed. Only the oriP-containing plasmids were found to replicate.

Figure 12:
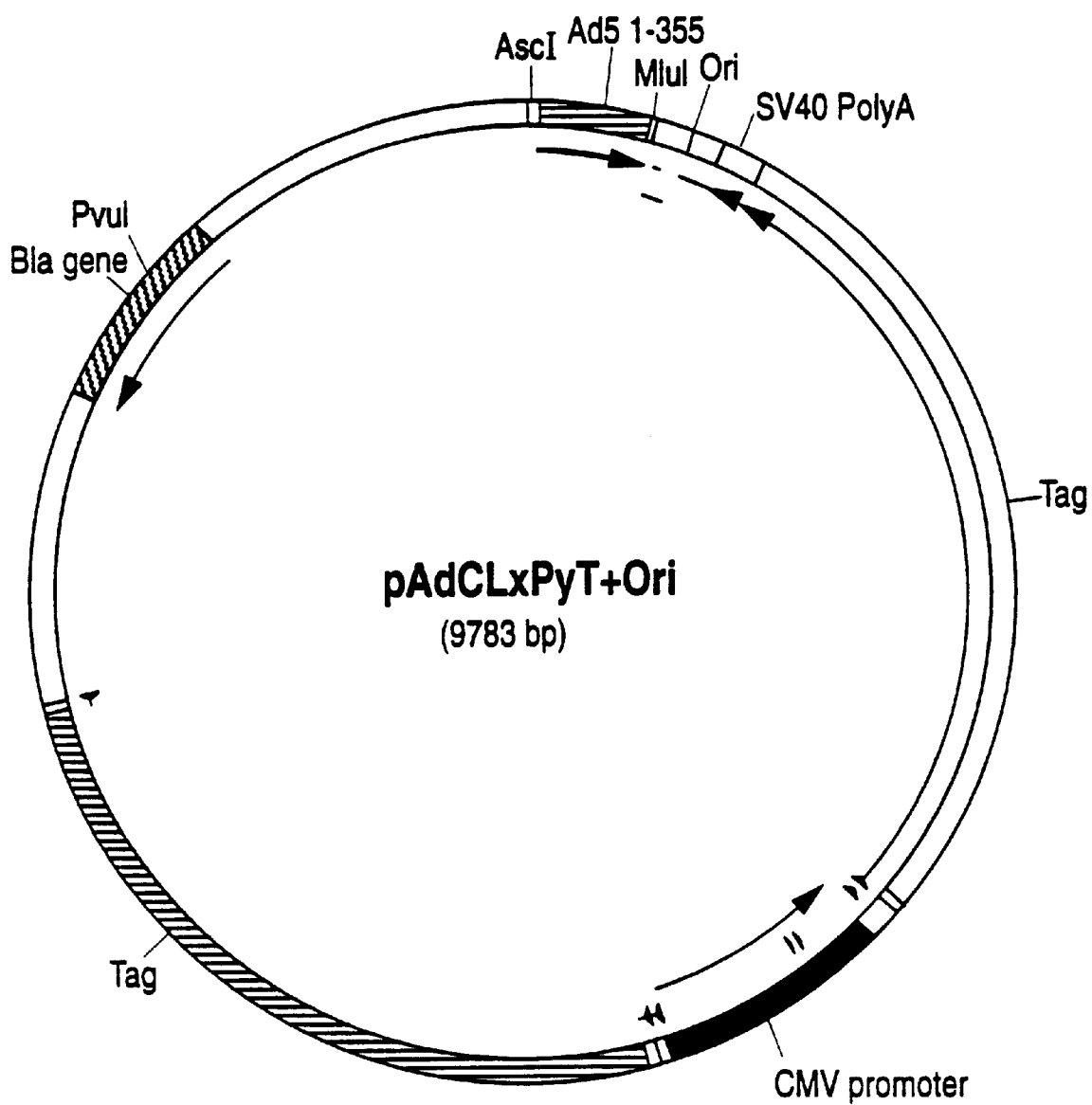
FIG. 12 is a restriction map depicting plasmid pAdCLx-PyTagOri.

Similarly, the plasmid pAdCLxPyTagOri (depicted in FIG. 12) was transfected into NIH 3T3 cells. This plasmid contains the polyomavirus large T antigen coding sequence under the control of the CMV promoter, and contains the polyomavirus origin immediately 3' of the polyadenylation signal flanking the T antigen coding sequence. A similar plasmid containing these elements except for the T antigen was found to replicate when T antigen was provided to the cell. These results thus confirm that the polyomavirus components present in this vector, like the EBV components present in pKSEBNAOriP(NR), is capable of imparting autonomous replication on a plasmid in which it is present.

Figure 13:
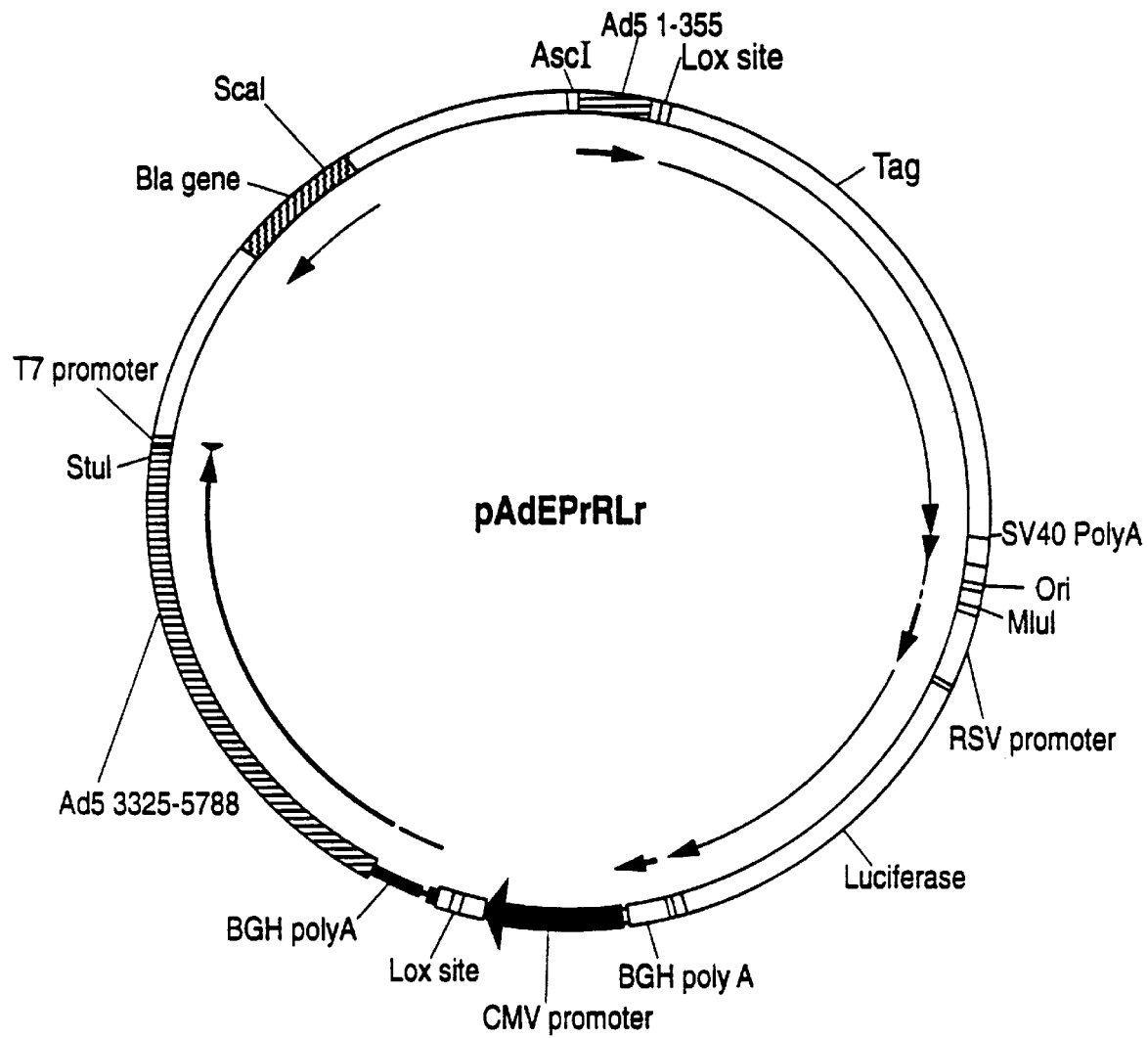
FIG. 13 is a restriction map depicting plasmid pAdEPrRlr.

Following confirmation of the Functioning of the polyomavirus components, the cassette present in pAdCLxPy-TagOri was transferred into the Ad E1 deletion shuttle vector pADEPrRLr depicted in FIG. 13. This plasmid is essentially as described in FIG. 1A with the first coding sequence (FCS) comprising the T antigen coding sequence and the operator being the polyomavirus origin of replication. The promoter (P) in this plasmid is an RSV promoter, and the second coding sequence (SCS) comprises a luciferase reporter gene. The activity of the luciferase transcriptional unit was confirmed. Moreover, transfection of this plasmid with a Cre expression cassette resulted in site-specific recombination of the shuttle vector. These results thus confirm the functionality of the various components of the vectors.

The results validate that other vectors for use for effecting site-specific recombination in a cell can be constructed and employed according to the invention. In particular, the results confirm that vectors that comprise a polyomavirus origin of replication can be constructed and used, for instance, to obtain runaway replication.

Example 5

This example describes further vectors for use for effecting site-specific recombination in a cell. In particular, this example describes vectors that comprise a bovine papillomavirus origin of replication and that can be used for obtaining a multicopy number in a wide variety of hosts.

Figure 14:
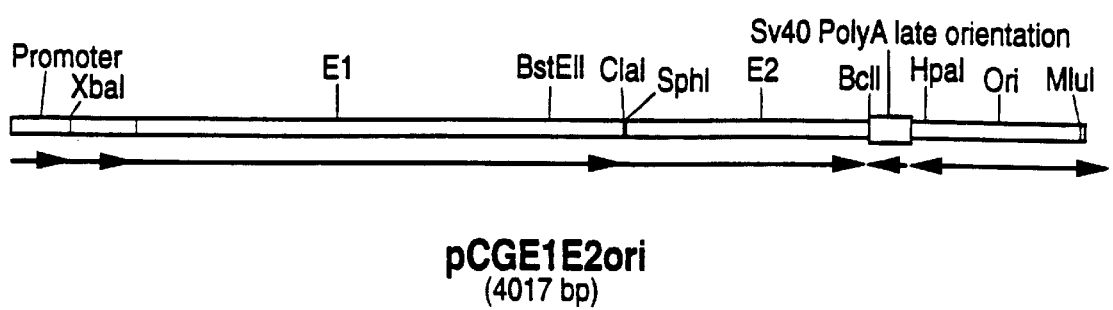
FIG. 14 is a restriction map depicting linearized plasmid pCGE1E2ori. The plasmid typically exists in closed-circular form.

Similar techniques as described in the earlier examples were employed to construct vectors comprising the bovine papillomavirus origin of replication. In particular, the vector pCGE1E2ori dEpicted in FIG. 14 was constructed. This vector comprises a dicistronic expression cassette with the bovine papilloma virus E1 and E2 genes under the control of a CMV promoter. Immediately, 3' of the expression cassette, the vector comprises the bovine papillomavirus origin of replication spanning nucleotides 7351–57 of the bovine papillomavirus genome. Another construct harboring the bovine papillomavirus origin previously was reported to be stably maintained in the presence of E1 and E2, which supports the replication competency of the pCGE1E2ori vector.

All of the references cited herein, including patents, patent applications, and publications, are hereby incorporated in their entireties by reference.

While this invention has been described with an emphasis upon preferred embodiments it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. A vector comprising:
   (i) a first recombining site and a second recombining site in parallel orientation, and
   (ii) one or more adeno-associated viral ITRs, wherein said vector optionally further comprises a passenger gene.

2. The vector of claim 1, which further comprises:
   (i) a promoter, which (a) is located in the region between said first and second recombining sites, (b) adjoins said second recombining site, and (c) is oriented to direct transcription in the direction from said first recombining site to said second recombining site proceeding through said promoter, and
   (ii) a coding sequence, which is located in the region between said first and second recombining sites, which comprises said promoter, adjoins said first recombining site, is oriented to be transcribed in the direction from said first recombining site to said second recombining site proceeding through said promoter, and is not operably linked to said promoter.

3. A method of effecting site-specific recombination in a eukaryotic cell, which method comprises:
   (a) contacting said cell with a vector of claim 2, such that said vector is internalized by said cell, and
   (b) providing said cell with a site-specific recombinase that effects recombination between said first and second recombining sites of said vector, wherein, upon recombination, said coding sequence is operably linked to said promoter.

4. The vector of claim 1, which further comprises:
   (i) a promoter, which (a) is located in the region between said first and second recombining sites, (b) adjoins said second recombining site, and (c) is oriented to direct transcription in the direction from said first recombining site to said second recombining site proceeding through said promoter, and
   (ii) a coding sequence, which is located in a region other than the region between said first and second recombining sites, which comprises said promoter, adjoins said second recombining site, and is operably linked to said promoter.

5. A method of effecting site-specific recombination in a eukaryotic cell, which method comprises:
   (a) contacting said cell with a vector of claim 4, such that said vector is internalized by said cell, and
   (b) providing said cell with a site-specific recombinase that effects recombination between said first and second recombining sites of said vector, wherein, upon recombination, said coding sequence is not operably linked to said promoter.

6. The vector of claim 1, which further comprises:
   (i) a promoter, which (a) is located in the region between said first and second recombining sites, (b) adjoins said first recombining site, and (c) is oriented to direct transcription in the direction from said first recombining site to said second recombining site proceeding through said promoter, and
   (ii) a coding sequence, which is located in a region other than the region between said first and second recombining sites, which comprises said promoter, adjoins said second recombining site, is oriented to be transcribed in the direction from said first recombining site to said second recombining site proceeding through said promoter, and is operably linked to said promoter.

7. A method of effecting site-specific recombination in a eukaryotic cell, which method comprises:
   (a) contacting said cell with a vector of claim 6, such that said vector is internalized by said cell, and
   (b) providing said cell with a site-specific recombinase that effects recombination between said first and second recombining sites of said vector, wherein, upon recombination, said coding sequence is not operably linked to said promoter.

8. The vector of claim 1, which further comprises:
   (i) a promoter, which is (a) located in a region other than the region between said first and second recombining sites, (b) adjoins said first recombining site, and (c) is oriented to direct transcription in the direction from said promoter to said second recombining site proceeding through said first recombining site, and
   (ii) a coding sequence, which is located in the region between said first and second recombining sites, adjoins said first recombining site, and is operably linked to said promoter.

9. A method of effecting site-specific recombination in a eukaryotic cell, which method comprises:
   (a) contacting said cell with a vector of claim 8, such that said vector is internalized by said cell, and
   (b) providing said cell with a site-specific recombinase that effects recombination between said first and second recombining sites of said vector, wherein, upon recombination, said coding sequence is not operably linked to said promoter.

10. The vector of claim 1, wherein said coding sequence, first coding sequence, second coding sequence or passenger gene comprises a sequence encoding a ligand binding domain of a hormone receptor that is capable of binding an exogenous, but not a naturally-occurring, hormone.

11. The vector of claim 1, wherein said coding sequence, first coding sequence, second coding sequence or passenger gene comprises one or more sequences encoding a glycine-alanine repeat.

12. A vector comprising:
   (i) a first recombining site and a second recombining site in parallel orientation,
   (ii) an origin of replication and/or one or more adeno-associated viral ITRs,
   (iii) one or more promoters, and
   (iv) one or more coding sequences,
   wherein, if said origin of replication is present, it is located between said first and second recombining sites,
   wherein, each of said one or more promoters and each of said one or more coding sequences adjoins the first or second recombining site, such that one or more of said first and second recombining sites is/are adjoined by one or more promoters and/or one or more coding sequences,
   wherein, upon recombination, upregulation of one or more coding sequence(s) and/or downregulation of one or more other coding sequence(s) is/are effected, and wherein said vector optionally further comprises a passenger gene.

13. The vector of claim 12, which comprises:
(i) a promoter, which (a) is located in the region between said first and second recombining sites, which, if the vector comprises an origin, comprises said origin, (b) adjoins said second recombining site, and (c) is oriented to direct transcription in the direction from said first recombining site to said second recombining site proceeding through said promoter, and
(ii) a coding sequence, which is located in the region between said first and second recombining sites, which comprises said promoter, adjoins said first recombining site, is oriented to be transcribed in the direction from said first recombining site to said second recombining site proceeding through said promoter, and is not operably linked to said promoter.

14. A method of effecting site-specific recombination in a eukaryotic cell, which method comprises:
(a) contacting said cell with a vector of claim 13, such that said vector is internalized by said cell, and, if the vector comprises an origin of replication, the origin of replication is functional in a mammalian cell, and
(b) providing said cell with a site-specific recombinase that effects recombination between said first and second recombining sites of said vector, wherein, upon recombination, said coding sequence is operably linked to said promoter.

15. The vector of claim 12, which comprises:
(i) a promoter, which (a) is located in the region between said first and second recombining sites, which, if the vector comprises an origin, comprises said origin, (b) adjoins said second recombining site, and (c) is oriented to direct transcription in the direction from said first recombining site to said second recombining site proceeding through said promoter, and
(ii) a coding sequence, which is located in a region other than the region between said first and second recombining sites, which comprises said promoter, adjoins said second recombining site, and is operably linked to said promoter.

16. A method of effecting site-specific recombination in a eukaryotic cell, which method comprises:
(a) contacting said cell with a vector of claim 15, such that said vector is internalized by said cell, and, if the vector comprises an origin of replication, the origin of replication is functional in a mammalian cell, and
(b) providing said cell with a site-specific recombinase that effects recombination between said first and second recombining sites of said vector, wherein, upon recombination, said coding sequence is not operably linked to said promoter.

17. The vector of claim 12, which comprises:
(i) a promoter, which (a) is located in the region between said first and second recombining sites, which, if the vector comprises an origin, comprises said origin, (b) adjoins said first recombining site, and (c) is oriented to direct transcription in the direction from said first recombining site to said second recombining site proceeding through said promoter, and
(ii) a coding sequence, which is located in a region other than the region between said first and second recombining sites, which comprises said promoter, adjoins said second recombining site, is oriented to be transcribed in the direction from said first recombining site to said second recombining site proceeding through said promoter, and is operably linked to said promoter.

18. A method of effecting site-specific recombination in a eukaryotic cell, which method comprises:
(a) contacting said cell with a vector of claim 17, such that said vector is internalized by said cell, and, if the vector comprises an origin of replication, the origin of replication is functional in a mammalian cell, and
(b) providing said cell with a site-specific recombinase that effects recombination between said first and second recombining sites of said vector, wherein, upon recombination, said coding sequence is not operably linked to said promoter.

19. The vector of claim 12, which comprises:
(i) a promoter, which is (a) located in a region other than the region between said first and second recombining sites, which, if the vector comprises an origin, comprises said origin, (b) adjoins said first recombining site, and (c) is oriented to direct transcription in the direction from said promoter to said second recombining site proceeding through said first recombining site, and
(ii) a coding sequence, which is located in the region between said first and second recombining sites, adjoins said first recombining site, and is operably linked to said promoter.

20. A method of effecting site-specific recombination in a eukaryotic cell, which method comprises:
(a) contacting said cell with a vector of claim 19, such that said vector is internalized by said cell, and, if the vector comprises an origin of replication, the origin of replication is functional in a mammalian cell, and
(b) providing said cell with a site-specific recombinase that effects recombination between said first and second recombining sites of said vector, wherein, upon recombination, said coding sequence is not operably linked to said promoter.

21. The vector of claim 12, wherein said coding sequence, first coding sequence, second coding sequence or passenger gene comprises a sequence encoding a ligand binding domain of a hormone receptor that is capable of binding an exogenous, but not a naturally-occurring, hormone.

22. The vector of claim 12, wherein said coding sequence, first coding sequence, second coding sequence or passenger gene comprises one or more sequences encoding a glycine-alanine repeat.

23. A method of effecting site-specific recombination in a eukaryotic cell, which method comprises:
(a) contacting said cell with a vector of claim 12, such that said vector is internalized by said cell, and, if the vector comprises an origin of replication, the origin of replication is functional in a mammalian cell, and
(b) providing said cell with a site-specific recombinase that effects recombination between said first and second recombining sites of said vector.

24. A vector comprising a first recombining site and a second recombining site in parallel orientation, between which are located (i) a first coding sequence, which adjoins said first recombining site such that said first coding sequence is oriented to be transcribed in the direction from said first recombining site to said second recombining site proceeding through said first coding sequence and which is not operably linked to a promoter, and (ii) a promoter, which adjoins said second recombining site such that said promoter is oriented to direct transcription in the direction from said first recombining site to said second recombining site proceeding through said promoter, wherein said vector optionally further comprises a passenger gene, an origin of replication located in the region between said first and second recombining sites comprising said first coding sequence, one or more adeno-associated viral ITRs, said passenger gene and said origin, or said passenger gene and said one or more adeno-associated viral ITRs.

25. The vector of claim 24, wherein said vector further comprises a second coding sequence, which is located in a region other than the region between said first and second recombining sites comprising said first coding sequence and which adjoins said second recombining site such that said second coding sequence is operably linked to said promoter.

26. The vector of claim 25, wherein said vector further comprises:
   (i) a splice acceptor site, which is located between said first recombining site and said first coding sequence such that splice acceptor site is in the region between said first and second recombining sites comprising said first coding sequence,
   (ii) a splice donor site, which is located between said promoter and said second recombining site such that said splice donor site is in the region between said first and second recombining sites comprising said first coding sequence, and
   (iii) a splice acceptor site, which is located between said second recombining site and second coding sequence such that said splice acceptor site is in a region other than the region between said first and second recombining sites comprising said first coding sequence.

27. A method of effecting site-specific recombination in a eukaryotic cell, which method comprises:
   (a) contacting said cell with a vector of claim 26, and
   (b) providing said cell with a site-specific recombinase that effects recombination between said first and second recombining sites of said vector.

28. A method of effecting site-specific recombination in a eukaryotic cell, which method comprises:
   (a) contacting said cell with a vector of claim 25, and
   (b) providing said cell with a site-specific recombinase that effects recombination between said first and second recombining sites of said vector, wherein, upon recombination, said second coding sequence is not operably linked to said promoter.

29. The vector of claim 24, wherein said vector further comprises:
   (i) a second coding sequence, which is located in a region other than the region between said first and second recombining sites, which comprises said first coding sequence and said promoter, adjoins said first recombining site such that said second coding sequence is oriented to be transcribed in the opposite direction from the direction of said first recombining site to said second recombining site proceeding through said first coding sequence, and is not operably linked to a promoter, and
   (ii) a second promoter, which is located in a region other than the region between said first and second recombining sites, which comprises said first coding sequence, and adjoins said second recombining site such that said second promoter is oriented to direct transcription in the opposite direction from the direction of said first recombining site to said second recombining site proceeding through said first coding sequence.

30. A method of effecting site-specific recombination in a eukaryotic cell, which method comprises:
   (a) contacting said cell with a vector of claim 29, and
   (b) providing said cell with a site-specific recombinase that effects recombination between said first and second recombining sites of said vector,
wherein, upon recombination, said first coding sequence is operably linked to said first promoter and said second coding sequence is operably linked to said second promoter.

31. The vector of claim 24, wherein said coding sequence, first coding sequence, second coding sequence or passenger gene comprises a sequence encoding a ligand binding domain of a hormone receptor that is capable of binding an exogenous, but not a naturally-occurring, hormone.

32. The vector of claim 24, wherein said coding sequence, first coding sequence, second coding sequence or passenger gene comprises one or more sequences encoding a glycine-alanine repeat.

33. A method of effecting site-specific recombination in a eukaryotic cell, which method comprises:
   (a) contacting said cell with a vector of claim 24, and
   (b) providing said cell with a site-specific recombinase that effects recombination between said first and second recombining sites of said vector, wherein, upon recombination, said first coding sequence is operably linked to said promoter.

34. A vector comprising:
   (i) a first recombining site and a second recombining site in parallel orientation between which is located a first coding sequence, which adjoins said first recombining site and is oriented to be transcribed in the direction from said first recombining site to said second recombining site proceeding through said first coding sequence,
   (ii) a promoter, which is located in a region other than the region between said first and second recombining sites, which comprises said first coding sequence, and adjoins said first recombining site such that said promoter is operably linked to said first coding sequence, and
   (iii) a second coding sequence, which is located in a region other than the region between said first and second recombining sites, which comprises said first coding sequence, adjoins said second recombining site, and is oriented to be transcribed in the direction from said first recombining site to said second recombining site proceeding through said first coding sequence,
wherein said vector optionally further comprises a passenger gene, an origin of replication located in the region between said first and second recombining sites comprising said first coding sequence, one or more adeno-associated viral ITRs, said passenger gene and said origin, or said passenger gene and said one or more adeno-associated viral ITRs.

35. The vector of claim 34, wherein said coding sequence, first coding sequence, second coding sequence or passenger gene comprises a sequence encoding a ligand binding domain of a hormone receptor that is capable of binding an exogenous, but not a naturally-occurring, hormone.

36. The vector of claim 34, wherein said coding sequence, first coding sequence, second coding sequence or passenger gene comprises one or more sequences encoding a glycine-alanine repeat.

37. A method of effecting site-specific recombination in a eukaryotic cell, which method comprises:
   (a) contacting said cell with a vector of claim 27, and
   (b) providing said cell with a site-specific recombinase that effects recombination between said first and second recombining sites of said vector, wherein, upon recombination, said first coding sequence is not operably linked to said promoter and said second coding sequence is operably linked to said promoter.

38. A vector comprising a first recombining site and a second recombining site in antiparallel orientation and one or more adeno-associated viral ITRs, wherein said vector optionally further comprises a passenger gene.

39. The vector of claim 38, which further comprises one or more promoters and one or more coding sequences,
   wherein, each of said one or more promoters and each of said one or more coding sequences adjoins the first or second recombining site, such that one or both of said first and second recombining sites is/are adjoined by one or more promoters and/or one or more coding sequences, and
   wherein, upon recombination, upregulation of one or more coding sequence(s) and/or downregulation of one or more other coding sequence(s) is/are effected.

40. The vector of claim 39, wherein said vector comprises:
   (i) a promoter, which is located in the region between said first and second recombining sites, adjoins said second recombining site, and is oriented to direct transcription in the direction from said first recombining site to said second recombining site proceeding through said promoter, and
   (ii) either a coding sequence "a", which is located in a region other than the region between said first and second recombining sites comprising said promoter, adjoins said first recombining site, is oriented to be transcribed in the opposite direction from the direction of said first recombining site to said second recombining site proceeding through said promoter, and is not operably linked to a promoter, or a coding sequence "b", which is located in a region other than the region between said first and second recombining sites comprising said promoter, adjoins said second recombining site, and is operably linked to said promoter.

41. A method of effecting site-specific recombination in a cell comprising:
   (a) contacting said cell with a vector of claim 40, such that said vector is internalized by said cell, and
   (b) providing said cell with a site-specific recombinase that effects recombination between said first and second recombining sites of said vector,
wherein, upon recombination, either said coding sequence "a" is operably linked to said promoter or said coding sequence "b" is not operably linked to said promoter.

42. The vector of claim 39, wherein said vector comprises:
   (i) a promoter, which is located in a region other than the region between said first and second recombining sites, adjoins said first recombining site and is oriented to direct transcription in the direction from said promoter to said second recombining site proceeding through said first recombining site, and
   (ii) either a coding sequence "a", which is located in the region between said first and second recombining sites, adjoins said first recombining site and is operably linked to said promoter, or a coding sequence "b", which is located in the region between said first and second recombining sites, adjoins said second recombining site, is oriented to be transcribed in the opposite direction from the direction of said first recombining site to said second recombining site proceeding through said coding sequence, and is not operably linked to said promoter.

43. A method of effecting site-specific recombination in a cell comprising:
   (a) contacting said cell with a vector of claim 42, such that said vector is internalized by said cell, and
   (b) providing said cell with a site-specific recombinase that effects recombination between said first and second recombining sites of said vector,
wherein, upon recombination, either said coding sequence "a" is not operably linked to said promoter or said coding sequence "b" is operably linked to said promoter.

44. A method of effecting site-specific recombination in a cell comprising:
   (a) contacting said cell with a vector of claim 39, such that said vector is internalized by said cell, and
   (b) providing said cell with a site-specific recombinase that effects recombination between said first and second recombining sites of said vector.

45. The vector of claim 38, wherein said coding sequence, first coding sequence, second coding sequence or passenger gene comprises a sequence encoding a ligand binding domain of a hormone receptor that is capable of binding an exogenous, but not a naturally-occurring, hormone.

46. The vector of claim 38, wherein said coding sequence, first coding sequence, second coding sequence or passenger gene comprises one or more sequences encoding a glycine-alanine repeat.

47. A method of effecting site-specific recombination in a cell comprising:
   (a) contacting said cell with a vector of claim 38, such that said vector is internalized by said cell, and
   (b) providing said cell with a site-specific recombinase that effects recombination between said first and second recombining sites of said vector.

48. A vector comprising:
   (i) a first recombining site and a second recombining site in anti-parallel orientation between which is located a promoter, which adjoins said second recombining site and is oriented to direct transcription in the direction from said first recombining site to said second recombining site proceeding through said promoter,
   (ii) a first coding sequence, which is in a region other than the region between said first and second recombining sites, which comprises said promoter, adjoins said first recombining site, is oriented to be transcribed in the opposite direction from the direction of said first recombining site to said second recombining site proceeding through said promoter, and is not operably linked to said promoter,
   (iii) a second coding sequence, which is in a region other than the region between said first and second recombining sites, which comprises said promoter, adjoins said second recombining site, and is operably linked to said promoter, and
   (iv) (a) one or more adeno-associated viral ITRs, (b) a passenger gene, or (c) one or more adeno-associated viral ITRs and a passenger gene.

49. The vector of claim 48, wherein said coding sequence, first coding sequence, second coding sequence or passenger gene comprises a sequence encoding a ligand binding domain of a hormone receptor that is capable of binding an exogenous, but not a naturally-occurring, hormone.

50. The vector of claim 48, wherein said coding sequence, first coding sequence, second coding sequence or passenger gene comprises one or more sequences encoding a glycine-alanine repeat.

51. A method of effecting site-specific recombination in a cell comprising:
- (a) contacting said cell with a vector of claim 48, such that said vector is internalized by said cell, and
- (b) providing said cell with a site-specific recombinase that effects recombination between said first and second recombining sites of said vector, wherein, upon recombination, said second coding sequence, which was operably linked to said promoter, is not operably linked to said promoter, and said first coding sequence, which was not operably linked to said promoter, is operably linked to said promoter.

52. A vector comprising:
- (i) a first recombining site and a second recombining site in anti-parallel orientation between which are located a first coding sequence, which adjoins said second recombining site and is oriented to be transcribed in the opposite direction from the direction of said first recombining site to said second recombining site proceeding through said first coding sequence, and a second coding sequence, which adjoins said first recombining site and is oriented to be transcribed in the direction of said first recombining site to said second recombining site proceeding through said second coding sequence,
- (ii) a promoter, which is in a region other than the region between said first and second recombining sites, which comprises said first and second coding sequences, adjoins said first recombining site, and is operably linked to said second coding sequence, and
- (iii) (a) one or more adeno-associated viral ITRs, (b) a passenger gene, or (c) one or more adeno-associated viral adeno-associated viral ITRs and a passenger gene.

53. The vector of claim 52, wherein said coding sequence, first coding sequence, second coding sequence or passenger gene comprises a sequence encoding a ligand binding domain of a hormone receptor that is capable of binding an exogenous, but not a naturally-occurring, hormone.

54. The vector of claim 52, wherein said coding sequence, first coding sequence, second coding sequence or passenger gene comprises one or more sequences encoding a glycine-alanine repeat.

55. A method of effecting site-specific recombination in a eukaryotic cell, which method comprises:
- (a) contacting said cell with a vector of claim 52, such that said vector is internalized by said cell, and
- (b) providing said cell with a site-specific recombinase that effects recombination between said first and second recombining sites of said vector.

56. A method of effecting site-specific recombination in a eukaryotic cell comprising:
- (a) contacting said cell with a vector comprising:
  - (i) a first recombining site and a second recombining site in parallel orientation, and
  - (ii) an origin of replication, which is located between said first and second recombining sites and is functional in a mammalian cell, and/or one or more adeno-associated viral ITRs, wherein said vector is internalized by said cell, and
- (b) providing said cell with a site-specific recombinase that effects recombination between said first and second recombining sites of said vector.

57. A vector comprising:
- (i) a first recombining site and a second recombining site,
- (ii) one or more adeno-associated viral ITRs, and
- (iii) minimal sequences required for packaging and delivery of the vector to a cell.

58. The vector of claim 57, wherein the minimal sequences required for packaging and delivery of the vector to a cell are derived from an adenovirus.

59. The vector of claim 58, wherein said vector is an adenoviral vector.

60. The vector of claim 57, wherein the vector further comprises a nucleic acid sequence encoding all or part of a Rep protein.

61. The vector of claim 57, wherein the vector comprises at least one passenger gene.

62. The vector of claim 61, wherein the vector further comprises regulatory sequences required for expression of the at least one passenger gene.

* * * * *

UNITED STATES PATENT AND TRADEMARK OFFICE
CERTIFICATE OF CORRECTION

PATENT NO. : 6,063,627
DATED : May 16, 2000
INVENTOR(S) : McVey, Duncan L. and Kovesdi, Imre It is certified that error appears in the above-identified patent and that said Letters Patent is hereby corrected as shown below:

> Claim 37, please change the dependency from "claim 27" to -- claim 34 --.

Signed and Sealed this

Twenty-seventh Day of February, 2001

*Attest:*

NICHOLAS P. GODICI

*Attesting Officer*   Acting Director of the United States Patent and Trademark Office